US008150507B2

(12) United States Patent
Hamaguchi et al.

(10) Patent No.: US 8,150,507 B2
(45) Date of Patent: Apr. 3, 2012

(54) BODY FAT MEASUREMENT DEVICE

(75) Inventors: Takehiro Hamaguchi, Kyoto (JP); Hiromichi Karo, Kyoto (JP); Shojiro Oku, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 61 days.

(21) Appl. No.: 12/598,336

(22) PCT Filed: May 20, 2008

(86) PCT No.: PCT/JP2008/059230
§ 371 (c)(1),
(2), (4) Date: Oct. 30, 2009

(87) PCT Pub. No.: WO2008/146663
PCT Pub. Date: Dec. 4, 2008

(65) Prior Publication Data
US 2010/0130885 A1    May 27, 2010

(30) Foreign Application Priority Data
Jun. 1, 2007 (JP) ................................. 2007-147372

(51) Int. Cl.
*A61B 5/05* (2006.01)
*A61B 5/00* (2006.01)
(52) U.S. Cl. ........................................ 600/547; 600/300
(58) Field of Classification Search .................... 600/547
See application file for complete search history.

(56) References Cited

U.S. PATENT DOCUMENTS
4,838,279 A * 6/1989 Fore .............................. 600/534
4,846,462 A * 7/1989 Regnier et al. .................... 482/1
6,487,445 B1 * 11/2002 Serita et al. .................. 600/547
6,640,460 B1 * 11/2003 Nabarro et al. ................. 33/759
(Continued)

FOREIGN PATENT DOCUMENTS
JP    2001-212093 A    8/2001
(Continued)

OTHER PUBLICATIONS

International Search Report w/translation from PCT/JP2008/059230 dated Jul. 1, 2008 (4 pages).
Patent Abstracts of Japan; Publication No. 2002-369806 datd Dec. 24, 2002; Kao Corp. (1 page).
(Continued)

*Primary Examiner* — Max Hindenburg
*Assistant Examiner* — Charles Becker
(74) *Attorney, Agent, or Firm* — Osha Liang LLP

(57) ABSTRACT

A body fat measurement device includes a bioelectrical impedance measurement body attachment unit with an electrode support and a belt. The belt includes a stretchable region at one part. The electrode support includes a fixing portion fixed with one end of the belt, and a holder for holding a portion closer to another end of the belt in a movable manner and including a wrapping length adjustment mechanism for adjusting the wrapping length thereof. The body fat measurement device includes a displacement amount detection unit for detecting a displacement amount of the belt caused by the stretching of the stretchable region, and a wrapping length adjustment mechanism control section for controlling the wrapping length adjustment mechanism based on information detected by the displacement amount detection unit. According to such a configuration, there is obtained a body fat measurement device including a bioelectrical impedance measurement abdomen attachment unit enabling smooth breathing motion without hardly giving pain to the subject, and capable of being closely attached with satisfactory reproducibility regardless of a waist length of the subject.

8 Claims, 15 Drawing Sheets

U.S. PATENT DOCUMENTS

| | | | |
|---|---|---|---|
| 6,766,272 B2 * | 7/2004 | Serita | 702/156 |
| 2005/0107717 A1 * | 5/2005 | Yamamoto et al. | 600/547 |
| 2006/0094978 A1 * | 5/2006 | Kodama | 600/547 |
| 2007/0038092 A1 * | 2/2007 | Jean-Claude et al. | 600/438 |
| 2007/0043302 A1 * | 2/2007 | Masuo | 600/547 |

FOREIGN PATENT DOCUMENTS

| | | |
|---|---|---|
| JP | 2002-369806 A | 12/2002 |
| JP | 2004-141186 A | 5/2004 |
| JP | 2005-118148 A | 5/2005 |
| JP | 2005-152061 A | 6/2005 |

OTHER PUBLICATIONS

Patent Abstracts of Japan; Publication No. 2005-118148 dated May 12, 2005; Omron Healthcare Co., Ltd. (1 page).

Patent Abstracts of Japan; Publication No. 2004-141186 dated May 20, 2004; Omron Healthcare Co., Ltd. (1 page).

Patent Abstracts of Japan; Publication No. 2001-212093 dated Aug. 7, 2001; Kyoto Kagaku:KK (1 page).

Patent Abstracts of Japan; Publication No. 2005-152061 dated Jun. 16, 2005; Matsushita Electric Works Ltd. (1 page).

* cited by examiner

BODY FAT MEASUREMENT DEVICE

TECHNICAL FIELD

The present invention relates to a body fat measurement device for calculating a body fat mass of a subject by measuring a bioelectrical impedance using a plurality of electrodes arranged in contact with a body of the subject, and in particular, to a body fat measurement device capable of individually calculating a visceral fat mass, a subcutaneous fat mass, and the like.

BACKGROUND ART

A body fat mass is recently being given attention as one index for knowing a health condition of a subject. In particular, a visceral fat mass is given attention as an index for making determination on whether or not a visceral fat obesity is present. The visceral obesity is said to induce lifestyle-related diseases that easily causes arterial sclerosis such as diabetes, a high blood pressure and hyperlipemia, and the use of the above index is expected from a standpoint of preventing such diseases. In this case, the visceral fat is a fat that accumulates around internal organs on an inner side of an abdominal muscle, and is distinguished from a subcutaneous fat that accumulates on a surface layer of the abdomen. An area (hereinafter referred to as visceral fat area) occupied by the visceral fat at a cross section of the abdomen of a portion corresponding to an umbilicus position is generally adopted for the index indicating the visceral fat mass.

Normally, an image analyzing method using a tomographic image of the abdomen photographed using an X-ray CT (Computer Tomography) or an MRI (Magnetic Resonance Imaging) is used to measure the visceral fat mass. In such an image analyzing method, the visceral fat area is calculated from the acquired tomographic image of the abdomen. However, in order to use such a method, a large facility that may be installed in medical institutions such as the X-ray CT and the MRI is required, and thus the visceral fat mass is very difficult to measure on a daily basis. A problem of exposure also arises when the X-ray CT is used, and thus such a method may not necessarily be a preferable measurement method.

As a measurement method taking the place thereof, application of a bioelectrical impedance method is being reviewed. The bioelectrical impedance method is a method of measuring the body fat mass widely used in a body fat measurement device for domestic use, where electrodes are brought into contact with four limbs, and the bioelectrical impedance is measured using such electrodes to calculate the body fat mass from the measured bioelectrical impedance. The above-described body fat measurement device accurately measures a degree of accumulation of the body fat by sites of the body such as the entire body or four limbs, or the body (trunk of the body), and is widely used in households and the like.

However, the conventional body fat measurement device measures the degree of accumulation of the body fat by sites of the body such as the entire body or four limbs, or the body (trunk of the body) as described above, and does not individually extract and accurately measure the degree of accumulation of the visceral fat or the degree of accumulation and the subcutaneous fat. This is because the body includes not only the visceral fat but also the subcutaneous fat, as described above, and thus accurately measuring the visceral fat mass and the subcutaneous fat mass individually is difficult in the body fat measurement device described above.

In order to solve such problems, consideration is being made of bringing an electrode directly in contact with the body, measuring the bioelectrical impedance using the electrode, and accurately measuring the visceral fat mass and the subcutaneous fat mass individually based thereon. For instance, Japanese Unexamined Patent Publication No. 2002-369806 (Patent Document 1) discloses a body fat measurement device configured such that the electrode is arranged in contact with the body by arranging an electrode on an inner peripheral surface of a belt member and wrapping and fixing the belt member to the body. The body fat measurement device disclosed in Japanese Unexamined Patent Publication No. 2002-369806 enables highly accurate measurement of the visceral fat mass and the subcutaneous fat mass, which has been difficult in the related art, by measuring the bioelectrical impedance using the electrode arranged in contact with the body of the subject using the belt member.

Patent Document 1: Japanese Unexamined Patent Publication No. 2002-369806

DISCLOSURE OF THE INVENTION

Problems to be Solved by the Invention

When measuring a bioelectrical impedance using the above-described bioelectrical impedance method, measurement is carried out by bringing an electrode directly in contact with a part of a body of a subject, and thus it is important to stably maintain a pressing strength of the electrode with respect to the body surface constant for every measurement. However, this is not easy to achieve as a shape and a size of the body of the subject differ among individuals. In particular, a difference among individuals is large in the shape and the size of the body, where stably ensuring the pressing strength of the electrode with respect to the body is very difficult when arranging the electrode so as to be in contact with the body of the subject using the bioelectrical impedance measurement body attachment unit including a belt member.

For instance, in the bioelectrical impedance measurement body attachment unit of the body fat measurement device disclosed in Japanese Unexamined Patent Publication No. 2002-369806, a wrapping strength of the belt member differs for every attachment as a attachment task of the belt member to the body is carried out manually, and thus the pressing strength of the electrode with respect to the body also differs for every attachment as a result.

In the case where the pressing strength of the electrode with respect to the body surface varies, such a variation appears as a variation of a contact resistance between the electrode and a body surface, which may lower the measurement accuracy. Therefore, it is very important that the bioelectrical impedance measurement body attachment unit is configured such that the electrode is always stably pressed against the body of the subject with a constant load regardless of the subject for every measurement.

On the other hand, in the case where the belt member is strongly wrapped around the body of the subject to ensure the pressing strength of the electrode with respect to the body, the body of the subject is tightened by the belt member, which may be painful to the subject. In particular, as the shape of the body (in particular, abdomen of the body) fluctuates with breathing motion (normally, a body peripheral length increases in inhaling motion and the body peripheral length reduces in exhaling motion), the user may feel a strong oppressing feeling in the inhaling motion, which may force great pain on the subject.

In the case where the bioelectrical impedance is measured with the electrode in contact with the body of the subject, a value of the measured bioelectrical impedance is known to fluctuate with the breathing motion of the subject. Major factors thereof being that the shape of the body changes with the breathing motion and a body composition between the electrodes arranged in contact with the body fluctuates, that the distance between the electrodes fluctuates with change in the shape of the body, that the contacting state of the electrode and the body surface fluctuates and the contact resistance changes, or the like. The fluctuation in the value of the bioelectrical impedance involved in such breathing motion inhibits the high accuracy measurement of a visceral fat mass and a subcutaneous fat mass, whereby some kind of measures needs to be taken.

In view of solving the above problems, it is an object of the present invention to provide a body fat measurement device equipped with a bioelectrical impedance measurement body attachment unit enabling smooth breathing motion without hardly giving pain to the subject in the attached state, and capable of being closely attached to the body of the subject at satisfactory reproducibility regardless of the body peripheral length of the subject.

In addition to the above object, it is also an object of the present invention to provide a body fat measurement device equipped with a bioelectrical impedance measurement body attachment unit enabling the electrode to be pressed against the body of the subject at a constant load with satisfactory reproducibility in the attached state.

In addition to the above object, it is also another object of the present invention to provide a body fat measurement device capable of detecting the breathing state of the subject at high accuracy, and thus measuring the body fat mass, in particular, the visceral fat mass and the subcutaneous fat mass at high accuracy.

Means for Solving the Problems

A body fat measurement device according to the present invention includes a bioelectrical impedance measurement body attachment unit, an impedance measuring portion, a body fat mass calculating portion, a displacement amount detection unit, and a wrapping length adjustment mechanism control section. The bioelectrical impedance measurement body attachment unit includes a plurality of electrodes arranged in contact with a body of a subject in an attached state, an electrode support for supporting the plurality of electrodes, and a long belt to be wrapped around the body of the subject in the attached state to attach the electrode support to the body of the subject. The belt includes, at least at one part, a stretchable region that stretches in a length direction. The electrode support includes a fixing portion fixed with one end of the belt in a relatively immovable manner with respect to the electrode support, and a holder for holding a portion closer to the other end of the belt in a relatively movable manner with respect to the electrode support. The holder includes a wrapping length adjustment mechanism for adjusting a wrapping length of the belt. The impedance measuring portion measures the bioelectrical impedance of the subject using the plurality of electrodes. The body fat mass calculating portion calculates the body fat mass of the subject based on the bioelectrical impedance measured by the impedance measuring portion. The displacement amount detection unit detects the displacement amount in the length direction of the belt caused by the stretching of the stretchable region. The wrapping length adjustment mechanism control section controls the wrapping length adjustment mechanism based on the information detected by the displacement amount detection unit to adjust the wrapping length of the belt.

According to such a configuration, the wrapping length of the belt can be adjusted by the wrapping length adjustment mechanism based on the displacement amount of the belt caused by the stretching of the stretchable region provided in the belt. Therefore, there is provided a body fat measurement device equipped with a bioelectrical impedance measurement body attachment unit enabling smooth breathing motion without hardly giving pain to the subject in the attached state and capable of being closely attached to the body of the subject with satisfactory reproducibility regardless of the body peripheral length of the subject by appropriately adjusting the wrapping length of the belt by the wrapping length adjustment mechanism.

In the body fat measurement device according to the present invention, the wrapping length adjustment mechanism control section preferably adjusts the wrapping length of the belt by controlling the wrapping length adjustment mechanism so that the displacement amount in the length direction of the belt caused by the stretching of the stretchable region becomes a predetermined value.

According to such a configuration, the body of the subject is always tightened with a constant tightening strength by the bioelectrical impedance measurement body attachment unit. Therefore, a body fat measurement device that enables the electrode to be pressed against the body of the subject with a constant load at satisfactory reproducibility in the attached state and that can calculate the body fat mass at high accuracy is obtained.

In the body fat measurement device according to the present invention, the wrapping length of the belt is preferably adjusted during an attachment task of attaching the bioelectrical impedance measurement body attachment unit to the body of the subject.

According to such a configuration, since the bioelectrical impedance measurement body attachment unit is attached to the body of the subject automatically with an optimum tightening strength, a body fat measurement device equipped with a bioelectrical measurement body attachment unit that greatly facilitates the attachment task and that excels in handability is obtained.

In the body fat measurement device according to the present invention, the wrapping length of the belt is preferably constantly adjusted during a measurement operation of the bioelectrical impedance.

According to such a configuration, the body of the subject is always tightened with a constant tightening strength by the bioelectrical impedance measurement body attachment unit during the measurement. Therefore, there is obtained a body fat measurement device that enables the electrode to be always pressed against the body of the subject with a constant load at satisfactory reproducibility during the measurement and that can calculate the body fat mass at high accuracy.

Preferably, the body fat measurement device according to the present invention further includes: a body peripheral length measurement unit for measuring a body peripheral length of the subject by detecting a wrapping length of the belt wrapped around the body of the subject with the bioelectrical impedance measurement body attachment unit attached to the body of the subject, and in this case, the body fat mass calculating portion preferably calculates the body fat mass of the subject based on the bioelectrical impedance measured by the impedance measuring portion and the body peripheral length of the subject measured by the body peripheral length measurement unit.

According to such a configuration, the body peripheral length of the subject can be easily and automatically measured by attaching the bioelectrical impedance measurement body attachment unit, and the body fat can be measured at high accuracy by calculating the body fat mass using the obtained body peripheral length.

Preferably, the body fat measurement device according to the present invention further includes: a body peripheral length fluctuation amount measurement unit for detecting fluctuation of a body peripheral length of the subject by detecting fluctuation of the wrapping length of the belt wrapped around the body of the subject with the bioelectrical impedance measurement body attachment unit attached to the body of the subject; and a breathing state detecting portion for detecting a breathing state of the subject based on the fluctuation of the body peripheral length of the subject measured by the body peripheral length fluctuation amount measurement unit; and in this case, the body fat mass calculating portion preferably calculates the body fat mass of the subject based on the bioelectrical impedance measured by the impedance measuring portion and information on the breathing state detected by the breathing state detecting portion.

According to such a configuration, the breathing state of the subject can be detected at high accuracy with a simple configuration of detecting the fluctuation of the wrapping length of the belt of the bioelectrical impedance measurement body attachment unit during the measurement. Through the use of such a detection method, the change in the body peripheral length of the subject involved in the breathing motion can be captured at high accuracy, and thus a body fat measurement device capable of calculating the body fat mass at high accuracy can be obtained.

In the body fat measurement device according to the present invention, the body fat calculating portion preferably extracts the bioelectrical impedance measured at a timing of transitioning from an exhaling motion to an inhaling motion detected by the breathing state detecting portion from time-series data of the bioelectrical impedance measured by the impedance measuring portion, and calculates the body fat mass of the subject from the extracted bioelectrical impedance.

According to such a configuration, the bioelectrical impedance can be measured excluding an influence of the fluctuation of the bioelectrical impedance that occurs with the breathing motion, and thus the body fat mass can be calculated at high accuracy.

In the body fat measurement device according to the present invention, the body fat mass calculating portion preferably includes a visceral fat mass calculating part for calculating a visceral fat mass of the subject.

The bioelectrical impedance needs to be measured with the electrodes arranged in contact with the body of the subject in order to measure the visceral fat mass at high accuracy, and thus the visceral fat mass can be particularly calculated at high accuracy with the body fat measurement device of the above configuration.

In the body fat measurement device according to the present invention, the body fat mass calculating portion preferably includes a subcutaneous fat mass calculating part for calculating a subcutaneous fat mass at an abdomen of the subject.

The bioelectrical impedance needs to be measured with the electrodes arranged in contact with the body of the subject in order to measure the subcutaneous fat mass at the abdomen at high accuracy, and thus the subcutaneous fat mass at the abdomen can be particularly calculated at high accuracy with the body fat measurement device of the above configuration.

Effects of the Invention

According to the present invention, there is provided a body fat measurement device equipped with a bioelectrical impedance measurement body attachment unit enabling smooth breathing motion without hardly giving pain to a subject in an attached state and capable of being closely attached to a body of the subject with satisfactory reproducibility regardless of a body peripheral length of the subject.

In addition to the above effects, according to the present invention, a body fat measurement device equipped with a bioelectrical impedance measurement body attachment unit that enables an electrode to be pressed against the body of the subject with a constant load at satisfactory reproducibility in the attached state is obtained.

In addition to the above effects, according to the present invention, a body fat measurement device that can detect a breathing state of the subject at high accuracy and that can measure a body fat mass, in particular, a visceral fat mass and a subcutaneous fat mass at high accuracy is obtained.

Figure 1:
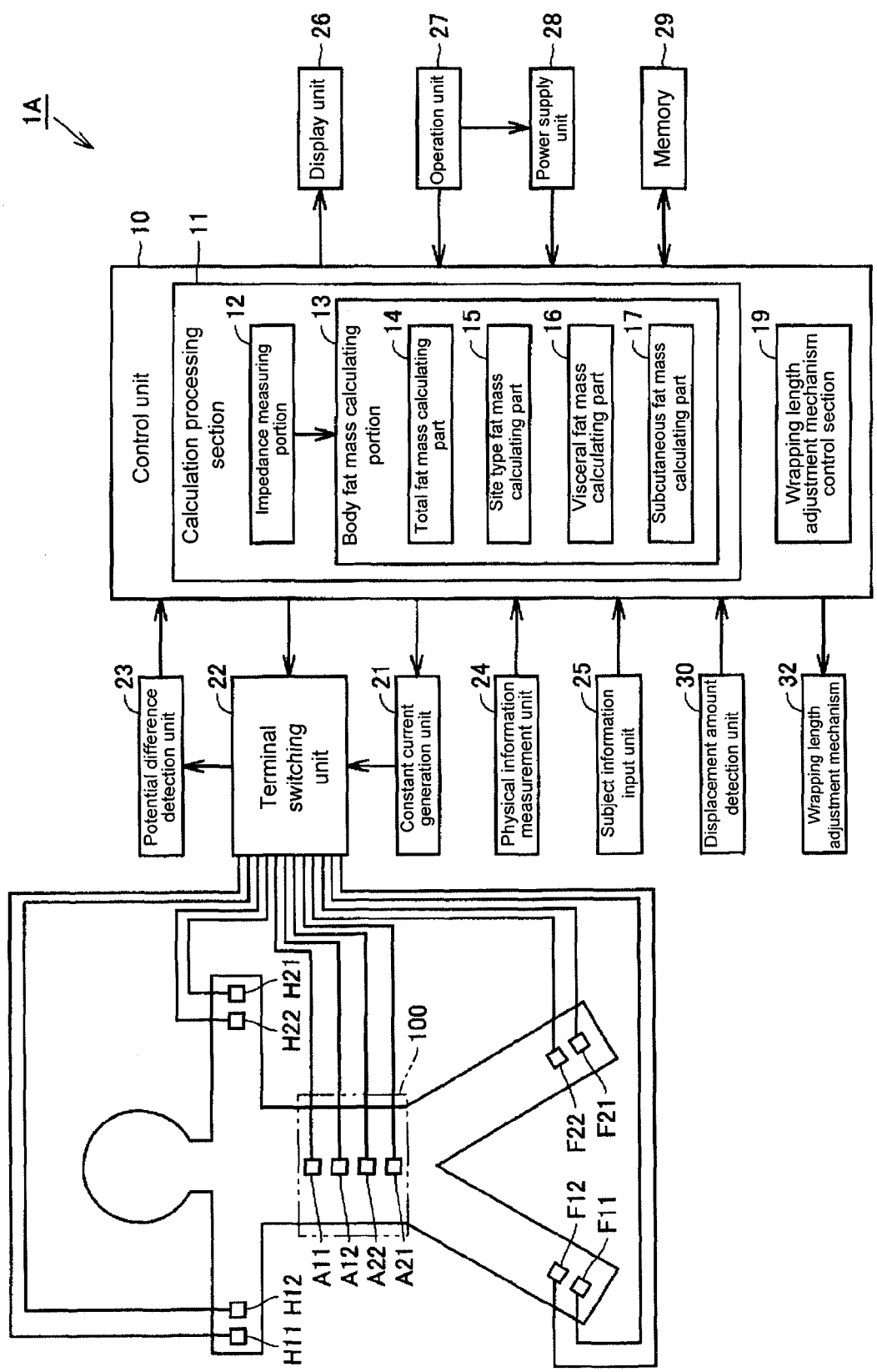
FIG. 1 is a view showing function blocks of a body fat measurement device according to a first embodiment of the present invention.

DESCRIPTION OF THE REFERENCE NUMERALS 1A, 1B body fat measurement device
10 control unit
11 calculation processing section
12 impedance measuring portion
13 body fat mass calculating portion
14 total fat mass calculating part
15 site type fat mass calculating part
16 visceral fat mass calculating part
17 subcutaneous fat mass calculating part
18 breathing state detecting portion
19 wrapping length adjustment mechanism control section
21 constant current generation unit
22 terminal switching unit
23 potential difference detection unit
24 physical information measurement unit
25 subject information input unit
26 display unit
27 operation unit
28 power supply unit
29 memory
30 displacement amount detection unit
32 wrapping length adjustment mechanism
34 waist length measurement unit
100 bioelectrical impedance measurement abdomen attachment unit
110 electrode support
111 sheet-like portion
112 electrode support mechanism accommodating portion
113 electrode
113a rod portion
113a1 collar portion
113b plate-shaped portion
114 fixing portion
116 guide frame
116a base body
116b lid body
117 coil spring
118 connector
119 positioning through-hole
120 holder
121 pulley with teeth
122 servo motor
123 rotation shaft
124 rotary encoder
125 detection shaft
126 photoelectronic sensor
130 displacement amount detection unit
131 movable iron core
132 detection coil
140 belt
141 one end
142 the other end
143 spring
144 encoder strip
145a, 145b barcode element
151 motor drive circuit
152 displacement amount detection circuit
153 waist length measurement circuit
165 device main body
172A, 172B bioelectrical impedance measurement upper limb attachment unit
173A, 173B bioelectrical impedance measurement lower limb attachment unit
180 connection cable
300 subject
301 abdomen
302A, 302B wrist
303A, 303B ankle
400 bed surface
A11, A12, A21, A22 abdominal electrode
F11, F12, F21, F22 lower limb electrode
H11, H12, H21, H22 upper limb electrode

BEST MODE FOR CARRYING OUT THE INVENTION

Embodiments of the present invention will be described in detail with reference to the drawings. The body fat measurement device in each embodiment described below is configured to include a bioelectrical impedance measurement abdomen attachment unit serving as a bioelectrical impedance measurement body attachment unit. The body fat measurement device in each embodiment described below is configured to be able to individually measure a visceral fat mass and a subcutaneous fat mass, but is also a body fat measurement device configured to be able to measure not only the visceral fat mass and the subcutaneous fat mass, but also a fat mass (total fat mass) of the entire body and a fat mass of a specific site of the body (fat mass of each of an upper limb and a lower limb, fat mass of the body, etc.).

First, prior to describing the body fat measurement device in each embodiment of the present invention, various terms representing the site of the body will be defined. "Body" refers to a portion excluding a head, a neck, and four limbs of the body, and a portion corresponding to a so-called trunk of the body including a chest and the abdomen. "Abdomen" refers to a portion positioned on the lower limb side when the body is divided to the portion positioned on the neck side (i.e., chest), and a portion positioned on the lower limb side, and includes an abdomen front surface and an abdomen rear surface. The "abdomen front surface" refers to a body surface of a portion visible when the subject is observed from the front surface side of the surface of the abdomen of the subject. The "abdomen rear surface" refers to a body surface of a portion visible when the subject is observed from the rear surface side of the surface of the abdomen of the subject. The "site distant from the abdomen" includes the upper limb including an upper arm, a forearm, a wrist, and fingers, the chest distant by greater than or equal to a predetermined distance (e.g., about 10 cm) from a portion where a diaphragm is positioned, the neck and the head, and the lower limb including a thigh, a lower thigh, an ankle, and toes. "Body axis" refers to an axis extending in a direction substantially perpendicular to a transverse section of the abdomen of the subject.

(First Embodiment)

FIG. 1 is a view showing function blocks of a body fat measurement device according to a first embodiment of the present invention. First, a configuration of function blocks of a body fat measurement device 1A according to the present embodiment will be described with reference to FIG. 1.

As shown in FIG. 1, a body fat measurement device 1A according to the present embodiment mainly includes a control unit 10, a constant current generation unit 21, a terminal switching unit 22, a potential difference detection unit 23, a physical information measurement unit 24, a subject information input unit 25, a display unit 26, an operation unit 27, a power supply unit 28, a memory 29, a displacement amount detection unit 30, a length adjustment mechanism 32, and a plurality of electrodes A11, A12, A21, A22, H11, H12, H21, H22, F11, F12, F21, and F22 attached to the body. The control unit 10 includes a calculation processing section 11 and a wrapping length adjustment mechanism control section 19. The calculation processing section 11 includes an impedance measuring portion 12, and a body fat mass calculating portion 13.

The control unit 10 is configured by a CPU (Central Processor Unit) and the like, and controls the overall body fat measurement device 1A. Specifically, the control unit 10 sends a command to the various types of function blocks described above or performs various types of calculation processes based on the obtained information. The various types of calculation processes are performed by the calculation processing section 11 arranged in the control unit 10.

The plurality of electrodes includes abdominal electrodes A11, A12, A21, A22 to be attached to the abdomen of the subject, upper limb electrodes H11, H12, H21, H22 to be attached to the upper limb of the subject, and lower limb electrodes F11, F12, F21, F22 to be attached to the lower limb of the subject.

The abdominal electrodes A11, A12, A21, A22 are arranged in the bioelectrical impedance measurement abdomen attachment unit 100 including a band-shaped member to be wrapped around the body of the part including the abdomen of the subject, and are attached to the surface of the abdomen of the subject with each electrode aligned along a body axis direction by attaching the bioelectrical impedance measurement abdomen attachment unit 100 to the abdomen of the subject. In this case, the abdominal electrodes A11, A12, A21, A22 may be attached to the abdomen front surface of the subject, or may be attached to the abdomen rear surface of the subject. An abdominal electrode group, where four abdominal electrodes A11, A12, A21, A22 form one set, may be attached to the abdomen in plural sets parallel to each other. In such a case, the abdominal electrode group of all of the sets may be attached to only one of either the abdomen front surface or the abdomen rear surface, or the abdominal electrode group of some sets may be attached to the abdomen front surface and the abdominal electrode group of the remaining sets may be attached to the abdomen rear surface. The details of the bioelectrical impedance abdomen attachment unit 100 including the abdominal electrodes A11, A12, A21, A22 will be described below.

The upper limb electrodes H11, H12, H21, H22 are attached to one of the sites of the upper limb corresponding to the site distant from the abdomen of the subject, and one pair thereof is suitably attached to the surface of the wrist of the right hand and the surface of the wrist of the left hand, respectively. The lower limb electrodes F11, F12, F21, F22 are attached to one of the sites of the lower limb corresponding to the site distant from the abdomen of the subject, and one pair thereof is suitably attached to the surface of the ankle of the right foot and the surface of the ankle of the left foot, respectively. The abdominal electrodes A11, A12, A21, A22, the upper limb electrodes H11, H12, H21, H22, and the lower limb electrodes F11, F12, F21, F22 are respectively electrically connected to the terminal switching unit 22.

The terminal switching unit 22 is configured by a relay circuit, and the like, and electrically connects a specific electrode selected from the plurality of electrodes and the constant current generation unit 21 and electrically connects a specific electrode selected from the plurality of electrodes and the potential difference detection unit 23 based on a command inputted from the control unit 10. Thus, the electrode electrically connected to the constant current generation unit by the terminal switching unit 22 functions as a constant current application electrode, and the electrode electrically connected to the potential difference detection unit 23 by the terminal switching unit 22 functions as a potential difference detection electrode. The electrical connection by the terminal switching unit 22 is switched in various manners during the measurement operation. Normally, the constant current application electrode and the potential difference detection electrode are respectively configured by a pair of electrodes, where each of the pair of electrodes as referred to herein includes both single electrode or a plurality of electrodes. In other words, each of the pair of electrodes can be configured by handling even the separately and independently arranged electrode in an electrically equivalent manner.

The constant current generation unit 21 generates a constant current based on a command inputted from the control unit 10, and supplies the generated constant current to the constant current application electrode through the terminal switching unit 22. A high frequency current (e.g., 50 kHz, 500 μA) suitably used to measure the body composition information is selected for the constant current generated in the constant current generation unit 21. Thus, the constant current is applied to the subject through the constant current application electrode.

The potential difference detection unit 23 detects a potential difference between the electrodes (i.e., potential difference detection electrode) electrically connected to the potential difference detection unit 23 by the terminal switching unit 22, and outputs the detected potential difference to the control unit 10. In this manner, the potential difference between the potential difference detection electrodes with the constant current applied to the subject is detected.

The physical information measurement unit 24 and the subject information input unit 25 are sites for obtaining subject information used in the calculation process performed in the body fat mass calculating portion 13 of the calculation processing section 11. The "subject information" refers to information related to the subject, and includes at least one of the information of age, sex, or physical information. The "physical information" includes information related to a size at a specific site of the body of the subject (e.g., information including at least one of body peripheral length (waist length) and abdomen lateral width, abdomen thickness, height, etc.), or information such as a weight. The physical information measurement unit 24 is a unit for automatically measuring the physical information of the subject, and outputs the detected physical information to the control unit 10. The subject information input unit 25 is a unit for inputting the subject information, and outputs the inputted subject information to the control unit 10.

In the function block diagram shown in FIG. 1, a case where both the physical information measurement unit 24 and the subject information input unit 25 are arranged in the body fat measurement device 1A has been described, but both the physical information measurement unit 24 and the subject information input unit 25 are not essential configurations. Whether or not to arrange the physical information measurement unit 24 and/or subject information input unit 25 is appropriately selected based on the type of subject information used in a calculation process performed in the calculation processing section 11 of the control unit 10. The physical information of the subject information may be automatically measured using the physical information measurement unit 24, and the measurement data may be used, or the subject himself/herself may input the information at the subject information input unit 25 without arranging the physical information measurement unit 24 and the input data may be used.

The calculation processing section 11 includes the impedance measuring portion 12 and the body fat mass calculating portion 13, as described above. The impedance measuring portion 12 calculates various types of bioelectrical impedances based on the current value of the constant current generated by the constant current generation unit 21, and the potential difference information inputted to the control unit 10 detected in the potential difference detection unit 23. The body fat mass calculating portion 13 calculates the body fat mass based on the bioelectrical impedance obtained by the impedance measuring portion 12 and the subject information inputted from the physical information measurement unit 24 and/or the subject information input unit 25. The body fat mass calculating portion 13 includes, for example, at least one of a total fat mass calculating part 14 for calculating the body fat mass of the entire body of the subject, a site type fat mass calculating part 15 for calculating the fat mass by specific site of the body of the subject, a visceral fat mass calculating part 16 for calculating the visceral fat mass of the subject, and a subcutaneous fat mass calculating part 17 for calculating the subcutaneous fat mass at the abdomen of the subject.

The display unit 26 displays information of various types of body fat mass calculated by the body fat mass calculating portion 13. An LCD (Liquid Crystal Display), and the like can be used for the display unit 26. The fat mass displayed on the display unit 26 may be total fat mass, i.e., the fat mass of the entire body of the subject, the site type fat mass, i.e., the fat mass of specific site of the body of the subject, the visceral fat mass, the subcutaneous fat mass at the abdomen, and the like. The "fat mass" refers to an index indicating the fat mass represented by a weight of fat, area of fat, volume of fat, fat level, and the like. In particular, the "visceral fat mass" refers to an index represented by at least one of a weight of visceral fat, area of visceral fat, volume of visceral fat, and visceral fat level; and the "subcutaneous fat mass" refers to an index represented by at least one of a weight of subcutaneous fat, area of subcutaneous fat, volume of subcutaneous fat, and subcutaneous fat level.

The operation unit 27 is a unit for the subject to input a command to the body fat measurement device 1A, and is configured by a key and the like that can be pushed by the subject.

The power supply unit 28 is a unit for supplying power to the control unit 10, and includes an internal power supply such as a battery and an external power supply such as a commercial power supply.

The memory 29 is a unit for storing various types of data and program related to the body fat measurement device 1A, and stores the subject information, the various types of calculated body fat mass, body fat measurement program for executing the body fat measurement process described below, and the like.

The displacement amount detection unit 30 is a unit for detecting a displacement amount in the length direction of the belt 140 (see FIG. 3 and the like, details will be described below) in the bioelectrical impedance measurement abdomen attachment unit 100, and outputting the detected displacement amount to the control unit 10.

The length adjustment mechanism 32 is a unit for adjusting the wrapping length of the belt 140 with respect to the abdomen of the subject, which operation is controlled by the wrapping length adjustment mechanism control section 19.

The wrapping length adjustment mechanism control section 19 controls the operation of the wrapping length adjustment mechanism 32 based on the information detected by the displacement amount detection unit 30. The wrapping length of the belt 140 with respect to the abdomen of the subject is thereby adjusted. Here, the "wrapping length of the belt with respect to the abdomen of the subject" is the length of the belt 140 at the portion that fits to the abdomen of the subject in the attached state of the entire length of the belt 140.

One example of the calculation process performed in the body fat measurement device 1A according to the present embodiment will now be described. As described above, various types of body fat mass can be measured by the body fat mass calculating portion 13 in the body fat measurement device 1A according to the present embodiment, where particularly described below by way of example is the calculation process performed when calculating the area of the visceral fat serving as an index indicating the visceral fat mass, the area of the subcutaneous fat serving as an index indicating the subcutaneous fat mass, and the body fat percentage serving as an index indicating the relationship of the body fat mass and the weight.

With reference to FIG. 1, the impedance measuring portion 12 calculates two types of bioelectrical impedances based on the current value of the constant current generated by the constant current generation unit 21 and the potential difference detected by the potential difference detection unit 23. One of the two types of bioelectrical impedances is a bioelectrical impedance Zt reflecting the fat free mass at the abdomen of the subject. The other bioelectrical impedance is a bioelectrical impedance Zs reflecting the subcutaneous fat mass at the abdomen of the subject.

The visceral fat mass calculating part 16 calculates a visceral fat area Sv (unit: $cm^2$) of the subject based on the calculated two types of impedances Zt, Zs, and a waist length W, which is one of the physical information of the subject. Specifically, the visceral fat area Sv is calculated by the following equation (1) expressing the relationship of the two types of impedances Zt, Zs and the waist length W of the subject, and the visceral fat area Sv.

$$Sv = a \times W^2 - b \times (1/Zt) - c \times W \times Zs - d \quad (1)$$

(where, a, b, c, d: coefficient)

The subcutaneous fat mass calculating part 17 calculates a subcutaneous fat area Ss (unit: $cm^2$) of the subject based on the calculated bioelectrical impedance Zs and the waist length W, which is one of the physical information of the subject. Specifically, the subcutaneous fat area Ss is calculated by the following equation (2) expressing the relationship of the bioelectrical impedance Zs and the waist length W of the subject, and the subcutaneous fat area Ss.

$$Ss = e \times W \times Zs + f \quad (2)$$

(where, e, f: coefficients)

The total fat mass calculating part 14 calculates a fat free mass FFM (unit: kg) based on the calculated bioelectrical impedance Zt and a height H, which is one of the physical information of the subject. Specifically, the fat free mass FFM is calculated by the following equation (3) expressing the relationship of the bioelectrical impedance Zt and the height H of the subject, and the fat free mass FFM.

$$FFM = i \times H^2/Zt + j \qquad (3)$$

(where i, j: coefficients)

The coefficients in each equation (1), (2), and (3) as above are defined by a regression equation based on the measurement result of an MRI. The coefficients in each equation (1), (2), and (3) may be defined by age and/or sex.

The total fat mass calculating part 14 calculates the body fat mass of the subject such as body fat percentage (%) based on the calculated fat free mass FFM and the weight Wt, which is physical information, when calculating the body fat mass of the entire body of the subject, although not directly related to the calculation of the visceral fat area Sv or the calculation of the subcutaneous fat area Ss. Specifically, for example, the body fat percentage is calculated by the following equation (4) based on the fat free mass FFM and the weight Wt of the subject.

$$\text{Body fat percentage} = (Wt - FFM)/Wt \times 100 \qquad (4)$$

Although the specific description will not be given, the body fat mass by sites of the body can be calculated based on the bioelectrical impedance, obtained by variously switching the current application electrode and the potential difference detection electrode, and the physical information of the subject.

Figure 2:
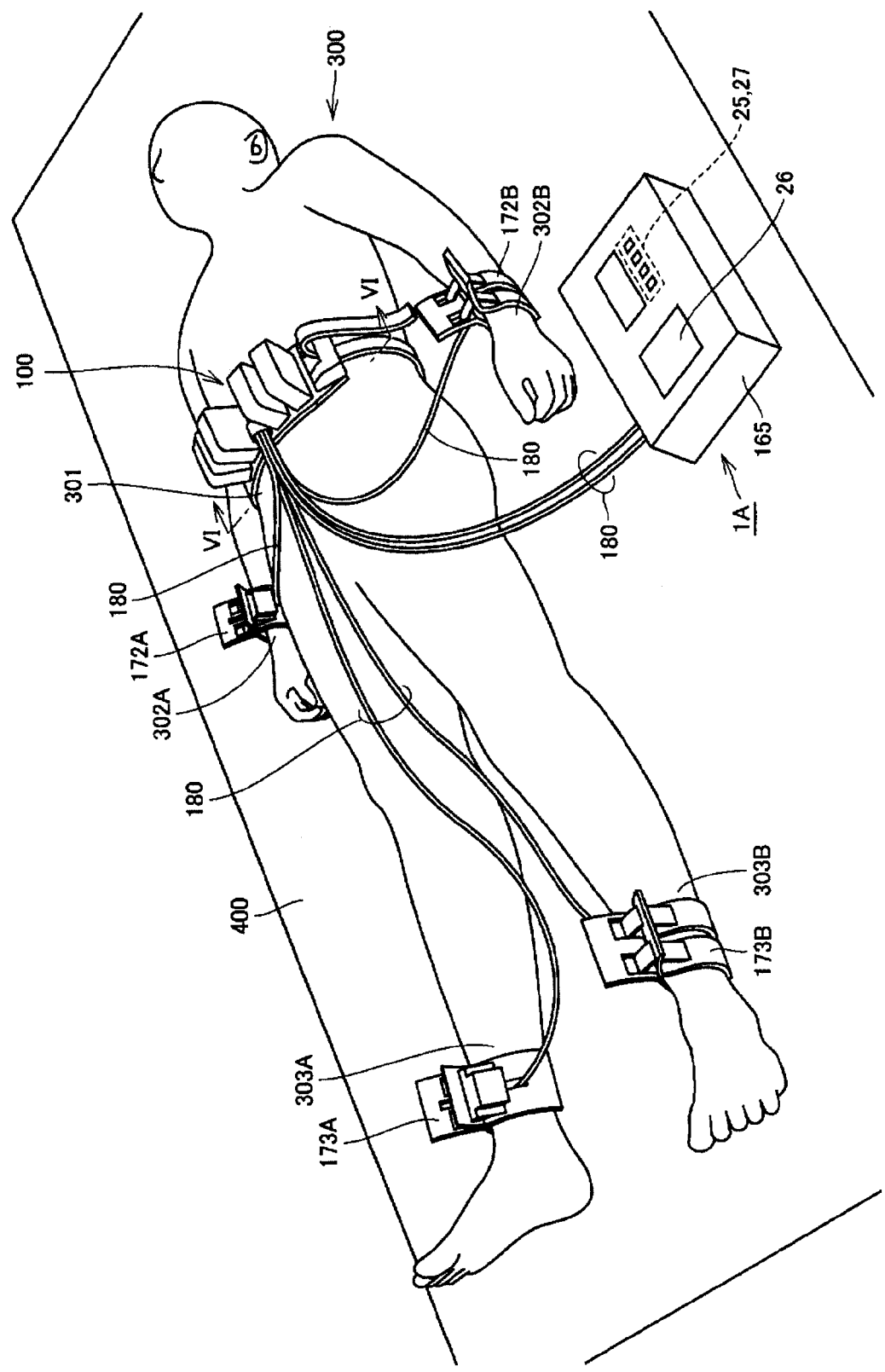
FIG. 2 is a flowchart showing operation procedures of the body fat measurement device in measuring a visceral fat area, a subcutaneous fat area, and a body fat percentage using the body fat measurement device according to the first embodiment of the present invention.

FIG. 2 is a view showing an outer appearance structure of the body fat measurement device according to the present embodiment, and is a perspective view showing a state where various types of attachment units arranged in the body fat measurement device are attached to the subject. An outer appearance structure of the body fat measurement device 1A according to the present embodiment and a posture to be taken by the subject in measurement will be described with reference to FIG. 2. The body fat measurement device 1A described below is configured with four sets of abdominal electrode groups, each set including four illustrated abdominal electrodes A11, A12, A21, A22, arranged parallel to each other in the body fat measurement device shown in FIG. 1.

Figure 3:
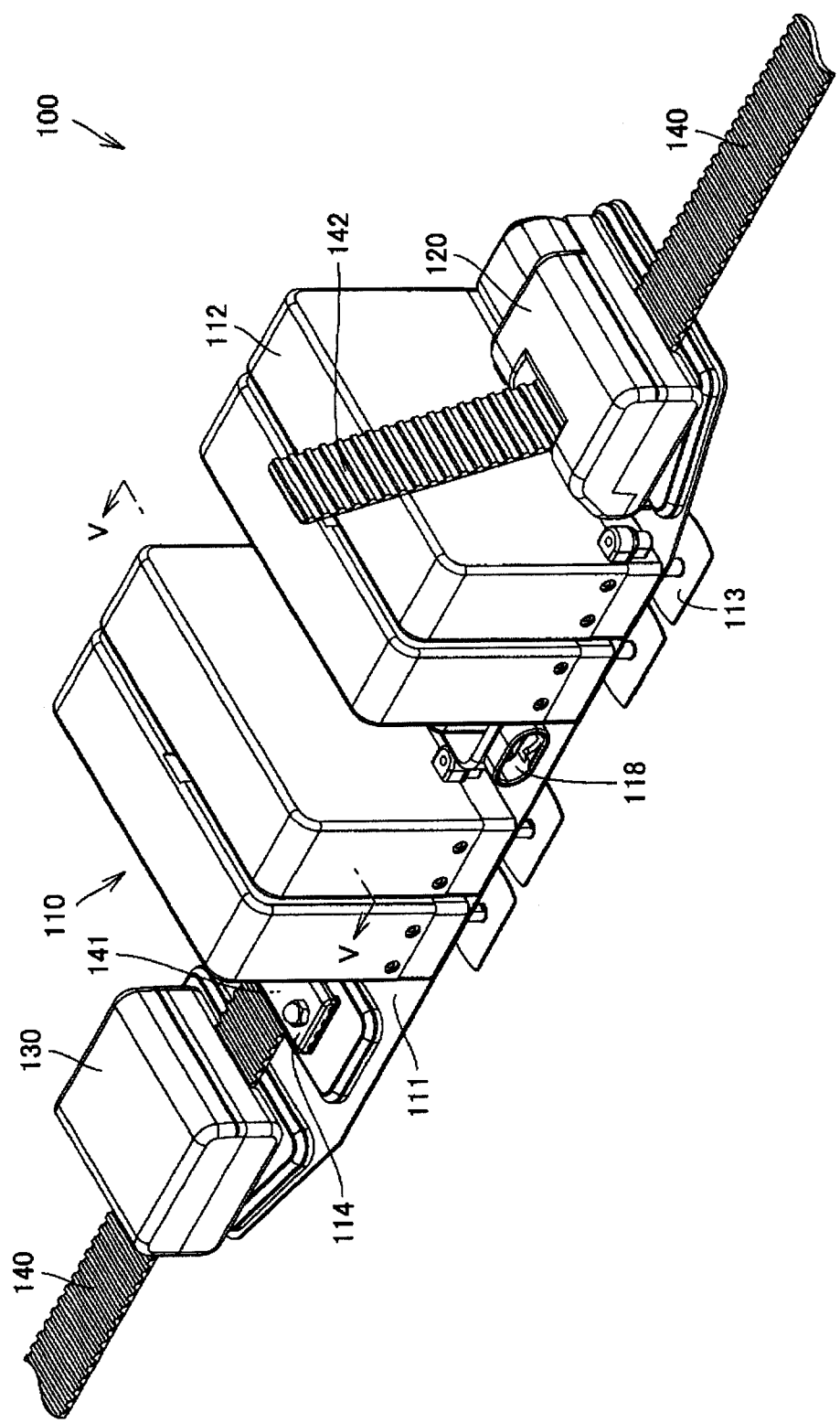
FIG. 3 is a perspective view showing an outer appearance structure of the bioelectrical impedance measurement abdomen attachment unit of the body fat measurement device according to the first embodiment of the present invention.

As shown in FIG. 3, the body fat measurement device 1A according to the present embodiment includes a bioelectrical impedance measurement abdomen attachment unit 100 to be attached to an abdomen 301 of a subject 300, a pair of bioelectrical impedance measurement upper limb attachment units 172A, 172B to be attached to the upper limb of the subject 300, a pair of bioelectrical impedance measurement lower limb attachment units 173A, 173B to be attached to the lower limb of the subject 300, and a device main body 165 connected to the various types of attachment units 100, 172A, 172B, 173A, 173B by way of a connection cable 180.

The bioelectrical impedance measurement abdomen attachment unit 100 is configured by a band-shaped member that can be wrapped around the abdomen 301. Each of the bioelectrical impedance measurement upper limb attachment units 172A, 172B and the bioelectrical impedance measurement lower limb attachment units 173A, 173B is configured by a clip-shaped member capable of sandwiching the upper limb or the lower limb of the subject 300. The bioelectrical impedance measurement abdomen attachment unit 100 includes abdominal electrodes (abdominal electrodes A11, A12, A21, A22 described above) capable of being arranged in contact with the surface of the abdomen of the subject. Each bioelectrical impedance measurement upper limb attachment unit 172A, 172B includes an upper limb electrode (upper limb electrodes H11, H12, H21, H22 described above) capable of being arranged in contact with the surface of the upper limb of the subject. Each bioelectrical impedance measurement lower limb attachment unit 173A, 173B includes a lower limb electrode (lower limb electrodes F11, F12, F21, F22 described above) capable of being arranged in contact with the surface of the lower limb of the subject.

The device main body 165 includes the control unit 10, the constant current generation unit 21, the terminal switching unit 22, the potential difference detection unit 23, the subject information input unit 25, the display unit 26, the operation unit 27, the memory 29, and the like. The constant current generation unit 21, the terminal switching unit 22, the potential difference detection unit 23, and the like arranged in the device main body 165 may be arranged in the bioelectrical impedance measurement abdomen attachment unit 100, as necessary. The displacement amount detection unit 30 and the wrapping length adjustment mechanism 32 are arranged in the bioelectrical impedance measurement abdomen attachment unit 100.

As shown in FIG. 2, when measuring various types of body fat mass, the subject 300 takes a laid position (i.e., posture of lying with face up) on a bed surface 400. The bioelectrical impedance measurement abdomen attachment unit 100 is attached to the abdomen 301 of the subject 300, the bioelectrical impedance measurement upper limb attachment units 172A, 172B are attached to the upper limb (suitably, wrists 302A, 302B) of the subject 300, and the bioelectrical impedance measurement lower limb attachment units 173A, 173B are attached to the lower limb (suitably, ankles 303A, 303B) of the subject 300. The electrodes arranged at the various types of attachment units 100, 172A, 172B, 173A, 173B are brought into contact with the body surface of the subject 300 by attaching the various types of attachment units 100, 172A, 172B, 173A, 173B. The subject 300 maintains the laid position during the measurement of various types of body fat mass.

Figure 4:
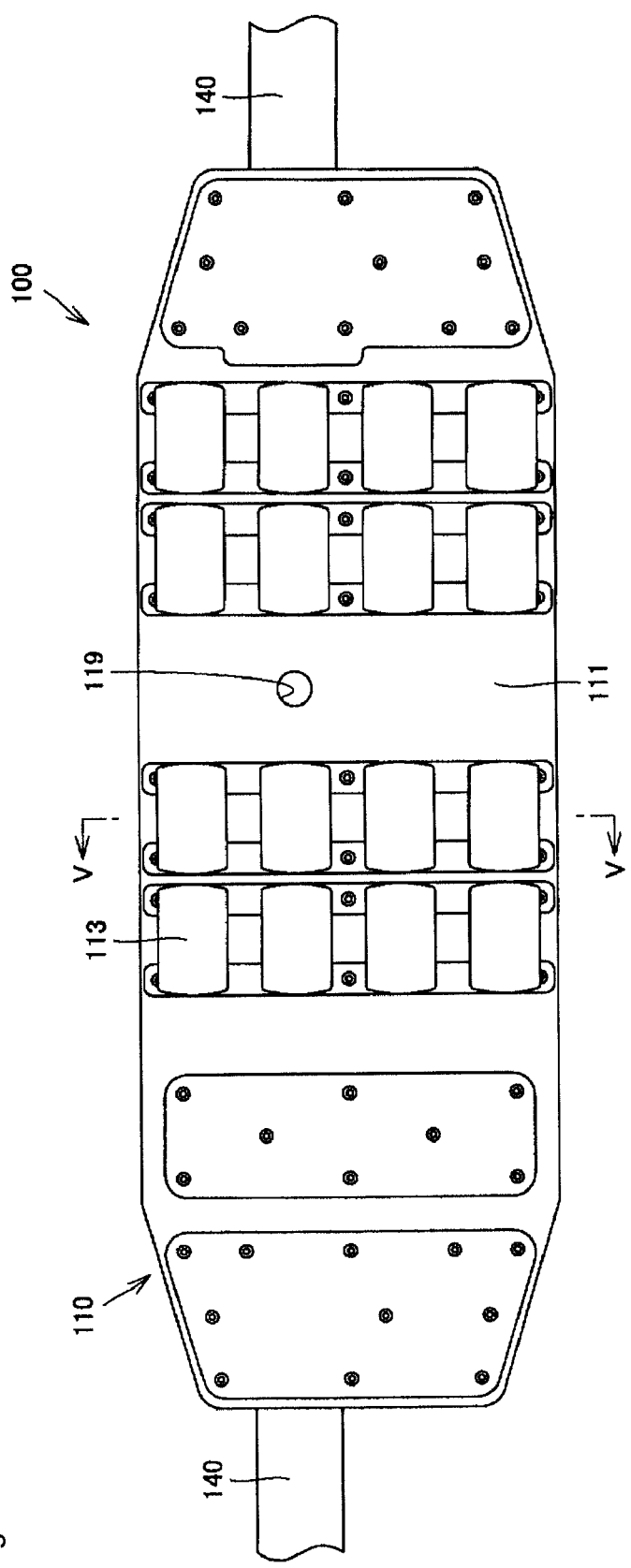
FIG. 4 is a bottom view showing the outer appearance structure of the bioelectrical impedance measurement abdomen attachment unit of the body fat measurement device according to the first embodiment of the present invention.
Figure 5:
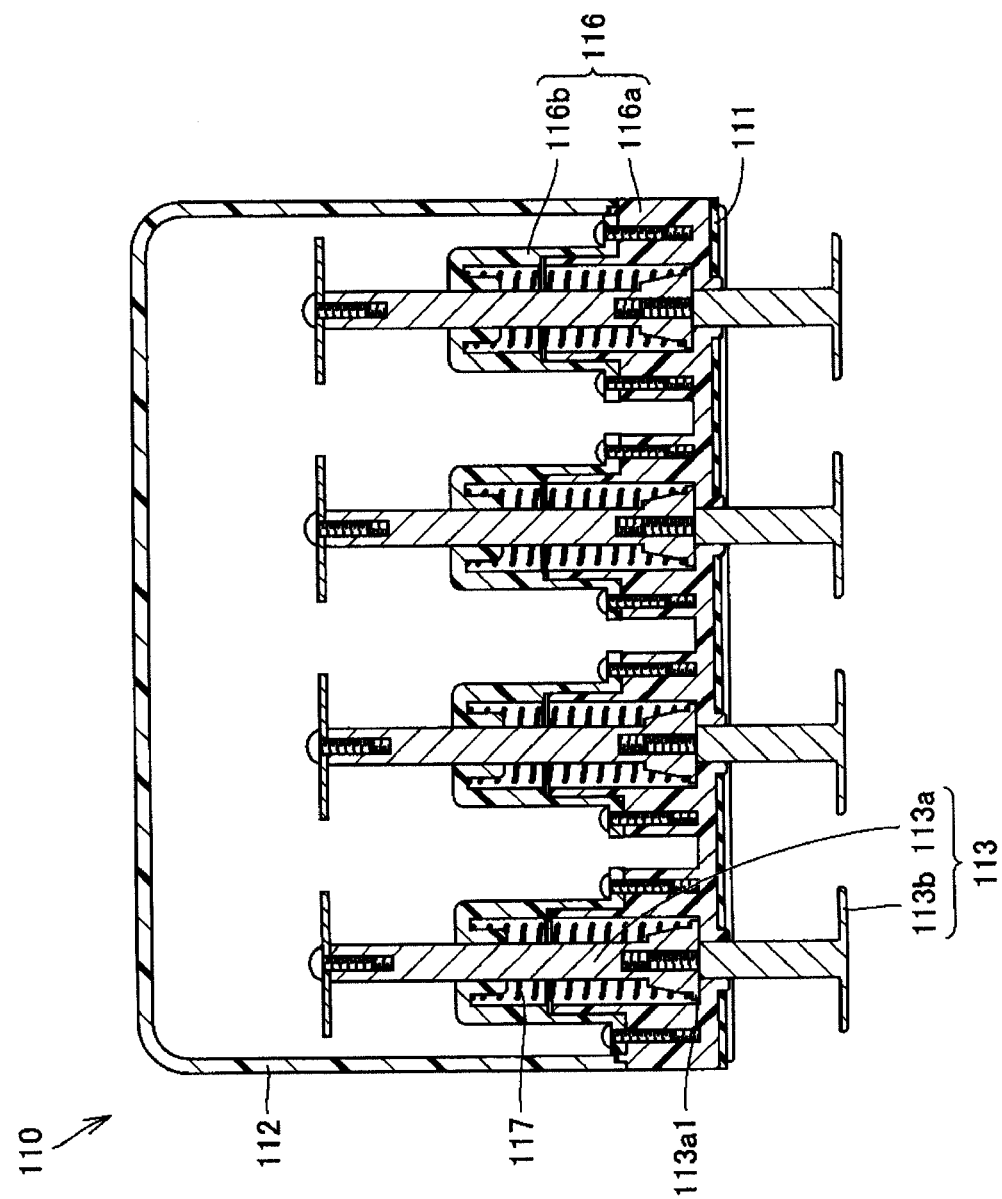
FIG. 5 is a cross-sectional view taken along line V-V shown in FIGS. 3 and 4 of the bioelectrical impedance measurement abdomen attachment unit shown in FIGS. 3 and 4.
Figure 6:
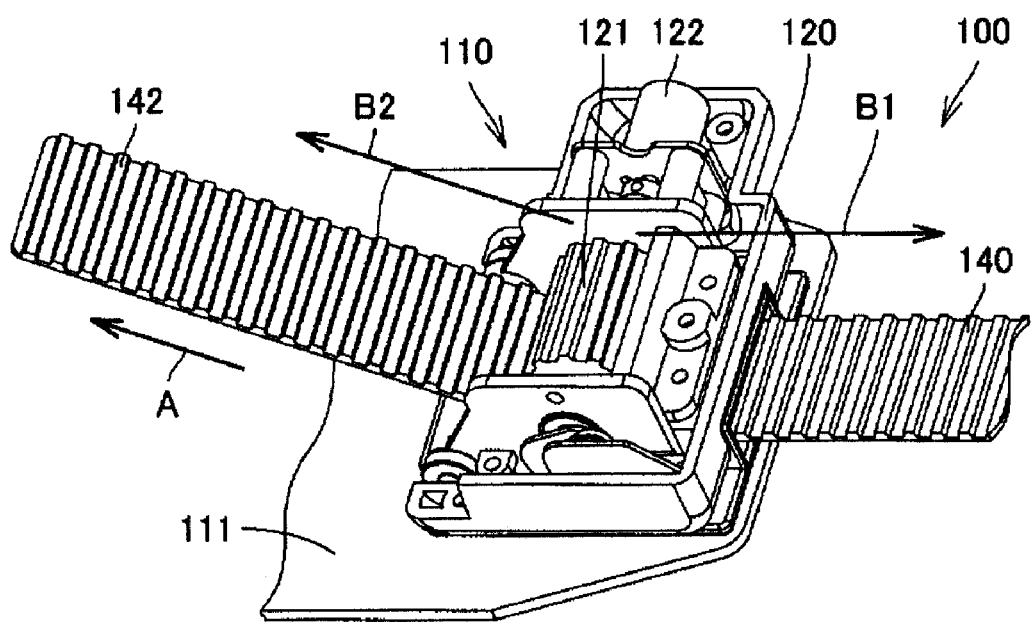
FIG. 6 is a perspective view describing a detailed structure of a holder of the bioelectrical impedance measurement abdomen attachment unit shown in FIGS. 3 and 4.

FIGS. 3 and 4 are views showing an outer appearance structure of the bioelectrical impedance measurement abdomen attachment unit of the body fat measurement device according to the present embodiment, where FIG. 3 is a perspective view and FIG. 4 is a bottom view. FIG. 5 is a cross-sectional view taken along line V-V shown in FIGS. 3 and 4 of the bioelectrical impedance measurement abdomen attachment unit shown in FIGS. 3 and 4. FIG. 6 is a perspective view for describing a detailed structure of a holder of the bioelectrical impedance measurement abdomen attachment unit shown in FIGS. 3 and 4. With reference to FIGS. 3 to 6, the structure of the bioelectrical impedance abdomen attachment unit of the body fat measurement device 1A according to the present embodiment will be described in detail, and a mechanism of holding the belt with the holder arranged in the bioelectrical impedance measurement abdomen attachment unit will be described. Note that, in FIG. 6, the illustration of a casing of the holder is partially not shown to facilitate the understanding.

As shown in FIGS. 3 and 4, the bioelectrical impedance measurement abdomen attachment unit 100 mainly includes an electrode support 110 and a belt 140. The electrode support 110 includes a sheet-like portion 111 including a sheet-like member having a substantially rectangular shape in plan view, an electrode support mechanism accommodating portion 112 arranged on an upper surface of the sheet-like portion 111, a plurality of electrodes 113 arranged so as to be partially exposed at the lower surface of the sheet-like portion 111, a fixing portion 114 and a displacement amount detection unit 130 arranged at one end in a length direction of the sheet-like portion 111, and a holder 120 arranged at the other end in the length direction of the sheet-like portion 111.

As shown in FIG. 3, one end 141 of the belt 140 is fixed so as to be relatively immovable with respect to the electrode support 110 by the fixing portion 114. The belt 140 is fixed with respect to the electrode support 110 by sandwiching the one end 141 of the belt 140 with the sheet-like portion 111 and a plate-shaped member which is screw fixed or the like to the sheet-like portion 111. The electrode support 110 and the belt 140 thereby configure the band-shaped member to be wrapped around the abdomen of the subject.

The displacement amount detection unit 130 is arranged at the portion on the more distal end side of the end on the side provided with the fixing portion 114 of the sheet-like portion 111. The displacement amount detection unit 130 is fixed so as to be relatively immovable with respect to the sheet-like portion 111. An insertion path for inserting the belt 140 is arranged at a predetermined position of the displacement amount detection unit 130, where the portion closer to the one end 141 of the belt 140 is inserted to the insertion path.

The sheet-like portion 111 is configured by a member that substantially does not have stretchability, and is made of a flexible material so as to fit to the surface of the abdomen of the subject in the attached state. The belt 140 has a long shape with a narrow width compared to the sheet-like portion 111, and is configured by a member that substantially does not have stretchability in the length direction other than the region of one part in the length direction. The exposed portion other than the portion inserted into the displacement amount detection unit 130 of the belt 140 is configured by a belt with teeth (timing belt) having teeth formed on one surface (main surface on the side not facing the abdomen of the subject in the attached state). The exposed portion of the belt 140 is made of a flexible material so as to fit to the surface of the abdomen of the subject in the attached state. A stretchable region that stretches in the length direction of the belt 140 is provided at the portion inserted to the displacement amount detection unit 130 of the belt 140. The detailed structure at the stretchable region and the portion in the vicinity thereof will be described below.

As shown in FIG. 5, each of the plurality of electrodes 113 arranged in the electrode support 110 includes a rod portion 113a that extends in a rod-shape, and a plate-shaped portion 113b arranged at the distal end of the rod portion 113a. The rod portion 113a is inserted to an insertion hole formed in the sheet-like portion 111. The plate-shaped portion 113b is exposed at the lower surface side of the sheet-like portion 111. The main surface on the side not coupled to the rod portion 113a of the plate-shaped portion 113b becomes the contacting surface that comes into contact with the abdomen of the subject. Each of the plurality of electrodes 113 is made of metal material excelling in biocompatibility. The plurality of electrodes 113 are arranged in a matrix form at the lower surface of the electrode support 110, where each of the electrodes 113 respectively corresponds to the abdominal electrodes A11, A12, A21, A22.

With reference to FIG. 3, the electrode support mechanism accommodating portion 112 is configured by a member having a box-shape, and interiorly includes an electrode support mechanism for movably supporting each of the plurality of electrodes 113 in a specific direction. The electrode support mechanism accommodating portion 112 is arranged for each of the four sets of abdominal electrode groups, where each set includes the abdominal electrodes A11, A12, A21, A22.

As shown in FIG. 5, the electrode support mechanism arranged in the interior of the electrode support mechanism accommodating portion 112 is configured by a guide frame 116 having a base body 116a fixed to the sheet-like portion 111 and a lid body 116b fixed to the base body 116a by a screw and the like, and a coil spring 117 arranged in a space formed in the interior of the guide frame 116. Each of the base body 116a and the lid body 116b configuring the guide frame 116 has an insertion hole, where the rod portion 113a of the electrode 113 is inserted and arranged in a hollow part of the coil spring 117 by inserting the rod portion 113a of the electrode 113 to the insertion hole. The coil spring 117 has one end in contact with the lid body 116b, and the other end in contact with a collar portion 113a1 formed at the rod portion 113a of the electrode 113. With this configuration, the plurality of electrodes 113 are thereby movably supported by the electrode support mechanism so as to be movable only in a direction substantially perpendicular to the surface of the abdomen of the subject in the attached state and biased towards the abdomen side by the biasing force of the coil spring 117.

As shown in FIGS. 3 and 6, a holder 120 is arranged at the other end in the length direction of the sheet-like portion 111 (end on the side not arranged with the fixing portion 114 and the displacement amount detection unit 130). The holder 120 is fixed so as to be relatively immovable with respect to the sheet-like portion 111. An insertion path for inserting the belt 140 is provided at a predetermined position of the holder 120. The holder 120 interiorly includes a servo motor 122, where a pulley with teeth 121 is attached to a rotation shaft 123 (see FIG. 8) of the servo motor 122.

The pulley with teeth 121 is arranged so as to face the insertion path provided in the holder 120, and to gear with the teeth of the belt 140 inserted to the insertion path. The holder 120 is fixed to the sheet-like portion 111, and holds the belt 140 in a manner of enabling entering and exiting of the belt 140. In other words, the holder 120 serves to hold the portion closer to the other end 142 of the belt 140 so as to be relatively movable with respect to the electrode support 110.

In order to hold the portion closer to the other end 142 of the belt 140 with the holder 120, the other end 142 of the belt 140 is inserted to the insertion path of the holder 120 in a direction of an arrow A in the figure. The teeth arranged at the inserted belt 140 thereby gear with the teeth of the pulley with teeth 121 arranged in the holder 120, so that the other end 142 of the belt 140 is held by the holder 120. Thereafter, the wrapping length of the belt 140 is adjusted using the wrapping length adjustment mechanism 32 so that the belt is tightened with an appropriate tightening strength with respect to the abdomen of the subject, where the detailed operation thereof will be described below.

As shown in FIG. 3, a connector 118 for attaching the connection cable 180 for relaying various types of attachment units 100, 172A, 172B, 173A, 173B and the device main body 165 is formed at the predetermined position of the sheet-like portion 111. As shown in FIG. 4, a positioning through-hole 119 aligned at an umbilicus position of the subject to position the electrode 113 with respect to the abdomen at the time of attachment is formed substantially at the central part of the sheet-like portion 111.

Figure 7:
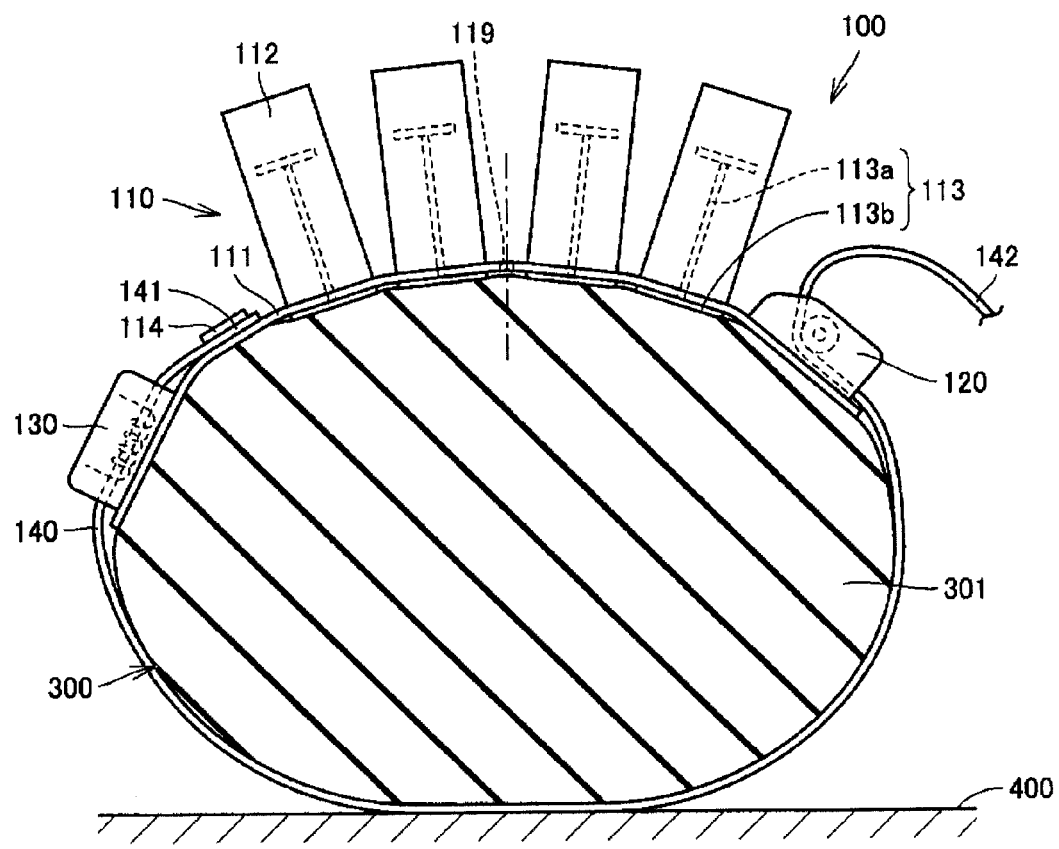
FIG. 7 is a schematic cross-sectional view showing a state where the bioelectrical impedance measurement abdomen attachment unit shown in FIGS. 3 and 4 is attached to an abdomen of a subject.

FIG. 7 is a schematic cross-sectional view showing a state where the bioelectrical impedance measurement abdomen attachment unit is attached to the abdomen of the subject. The state where the bioelectrical impedance measurement abdomen attachment unit of the body fat measurement device 1A according to the present embodiment is attached to the abdomen of the subject will be described with reference to FIG. 7.

As shown in FIG. 7, in the state where the bioelectrical impedance measurement abdomen attachment unit 100 is attached to the abdomen 301 of the subject 300, the bioelectrical impedance measurement abdomen attachment unit 100 including a band-shaped member is attached in a wrapped-around state to the abdomen 301 of the subject 300. At the time of attachment, the electrode support 110 is positioned and placed on the abdomen 301 of the subject so that the positioning through-hole 119 formed in the electrode support 110 matches the umbilicus position of the subject 300, and the belt 140 is wrapped around the flank and the rear surface of the abdomen of the subject 300 in the positioned state. The bioelectrical impedance measurement abdomen attachment unit 100 is attached to the abdomen 301 of the subject 300 by holding the portion closer to the other end 142 of the belt 140 with the holder 120 arranged at the electrode support 110. In this manner, the plurality of electrodes 113 arranged on the lower surface side (inner peripheral surface side in the attached state) of the electrode support 110 are arranged in contact with the front surface of the abdomen of the subject 300.

Figure 8:
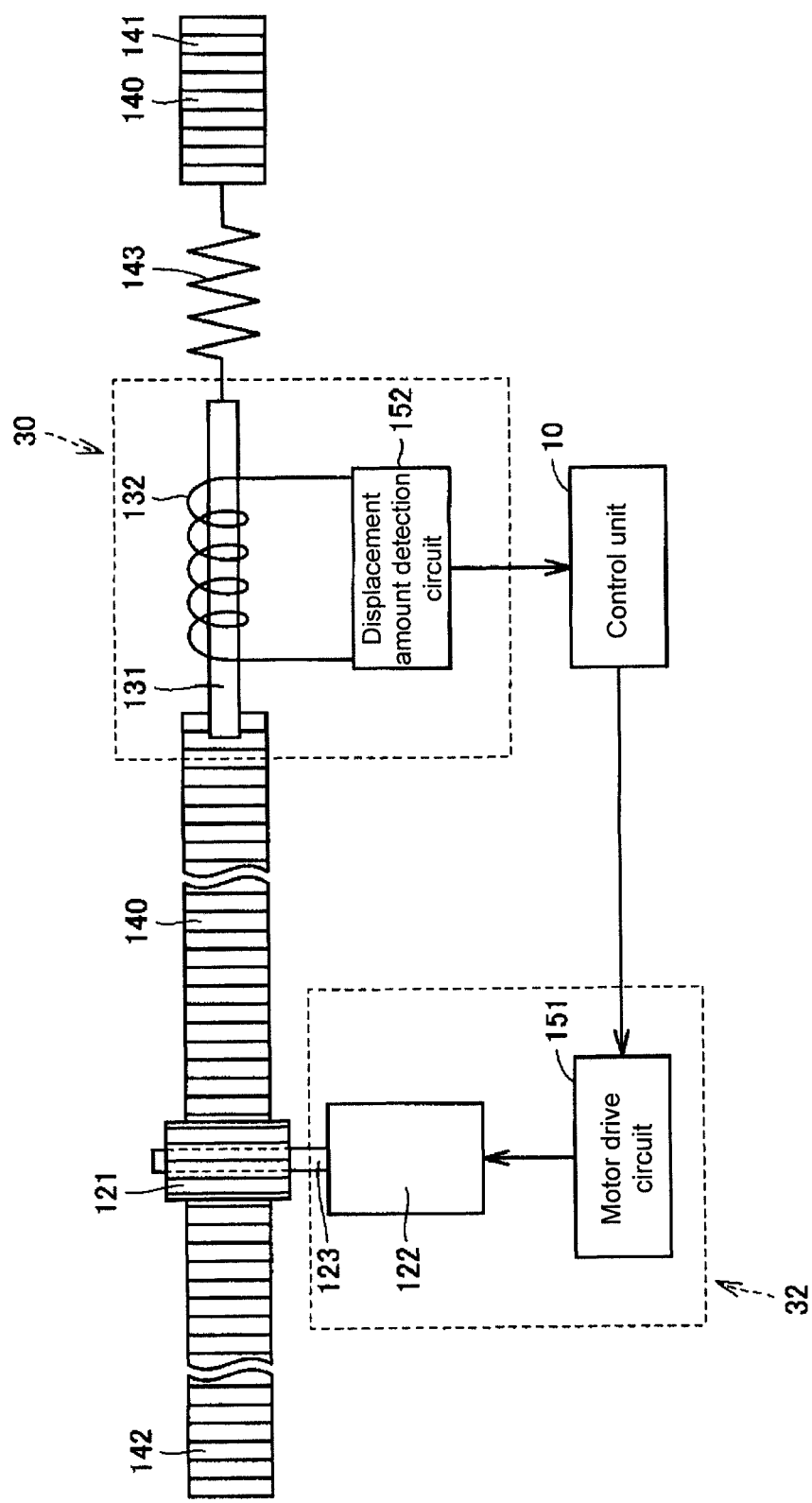
FIG. 8 is a function block diagram showing a specific configuration of a displacement amount detection unit and a wrapping length adjustment mechanism of the body fat measurement device according to the first embodiment of the present invention.

FIG. 8 is a function block diagram showing a specific configuration of the displacement amount detection unit and the wrapping length adjustment mechanism of the body fat measurement device according to the present embodiment. The specific configuration of the displacement amount detection unit and the wrapping length adjustment mechanism of the body fat measurement device 1A according to the present embodiment will be described below with reference to the figure.

As shown in FIG. 8, the belt 140 wrapped around the abdomen of the subject is divided in half at a predetermined position. The belt that is divided in half is coupled by a movable iron core 131 and a spring 143 arranged in between. Specifically, the movable iron core 131 and the spring 143 are connected in series, where both ends of a member including the movable iron core 131 and the spring 143, which are connected in series, are connected to the respective ends of the belt divided in half, so that the belt divided in half is coupled by the movable iron core 131 and the spring 143.

More specifically, of the belt divided in half, one end of the spring 143 is connected to the belt including the one end 141 fixed to the electrode support 110 by the fixing portion 114, and one end of the movable iron core 131 is connected to the other belt. The movable iron core 131 and the spring 143 are arranged inside the displacement amount detection unit 130, where the spring 143 forms the stretchable region of the belt 140. Therefore, the stretchable region of the belt 140 is elastically deformable in the length direction.

The displacement amount detection unit 30 includes the movable iron core 131 arranged at a position in the middle of the belt 140, a detection coil 132 wound and arranged to enable the movable iron core 131 to be inserted therethrough, and a displacement amount detection circuit 152 electrically connected to the detection coil 132. The displacement amount detection circuit 152 detects the displacement amount of the movable iron core 131 by flowing a high frequency current to the detection coil 132, and detecting the fluctuation of the impedance that occurs when the movable iron core 131 moves through the detection coil 132 in the inserted direction. The displacement amount of the movable iron core 131 detected by the displacement amount detection circuit 152 is inputted to the control circuit 10.

The wrapping length adjustment mechanism 32 includes the servo motor 122 arranged in the holder 120, and a motor drive circuit 151 for controlling the operation of the servo motor 122. The motor drive circuit 151 controls the operation of the servo motor 122 based on the command from the wrapping length adjustment mechanism control section 19 of the control unit 10. More specifically, the motor drive circuit 151 adjusts the electrical signal to input to the servo motor 122 (e.g., adjust magnitude of drive voltage and drive current) to switch the rotating direction of the rotation shaft 123 of the servo motor 122 in the forward direction/reverse direction, and adjust the amount of rotation.

The wrapping length of the belt 140 with respect to the abdomen 301 of the subject 300 can be automatically adjusted based on the detected displacement amount of the belt 140 by adopting the above configuration. In other words, the displacement amount of the belt 140 detected by the displacement amount detection unit 30 is inputted to the control unit 10, the wrapping length adjustment mechanism control section 19 drives and controls the servo motor 122 based on the information of the inputted displacement amount, and sends the belt 140 in the direction of the arrow B1 or B2 shown in FIG. 6 in the holder 120. In this manner, the holding position of the belt 140 in the holder 120 is adjusted, and the wrapping length of the belt 140 with respect to the abdomen 301 of the subject 300 is adjusted.

In this case, the belt 140 can always be wrapped around the abdomen 301 of the subject 300 with a constant wrapping strength by controlling the wrapping length of the belt 140 such that the displacement amount detected by the displacement amount detection unit 30 is always a predetermined value defined in advance. Thus, a plurality of electrodes 113 can always be pressed against the abdomen 301 of the subject 300 with a constant load by the bioelectrical impedance measurement abdomen attachment unit 100. In this case, the predetermined value is set as a value at which the electrode 113 is pressed against the abdomen 301 of the subject 300 at an optimum load suited for measurement, so that the electrode 113 is always pressed against the abdomen 301 of the subject 300 with an optimum pressing strength during the measurement. The tensile load applied on the band-shaped member including the sheet-like portion 111 and the belt 140 when the pressing strength of the electrode 113 against the abdomen 301 of the subject 300 is optimized is between about 1.0 kgf and 2.0 kgf, and preferably 1.5 kgf.

The automatic adjustment of the wrapping length of the belt 140 with respect to the abdomen 301 of the subject 300 is preferably performed both during the attachment task of attaching the bioelectrical impedance measurement abdomen attachment unit 100 to the abdomen 301 of the subject 300, and during the measurement operation of the bioelectrical impedance. In other words, during the attachment task, the wrapping length is automatically adjusted after inserting the other end 142 of the belt 140 to the holder 120, so that the excessive portion of the belt 140 is sent by the servo motor 122 in the direction of the arrow B2 shown in FIG. 6, and the belt 140 is closely attached to the abdomen 301 of the subject 300 and wrapped around the abdomen 301 of the subject 300 with an appropriate tightening strength. During the measurement operation, the belt 140 is always wrapped around the abdomen 301 of the subject 300 with an appropriate tightening strength by adjusting the wrapping length of the belt 140 with respect to the abdomen 301 of the subject 300 with the fluctuation of the waist length involved in the breathing motion of the subject 300.

In the above description, a configuration in which the belt divided in half is connected using the movable iron core 131 and the spring 143, which are connected in series, has been described by way of example for the connection structure of the belt divided in half, but other connection structures may also be adopted. For instance, the belt divided in half may be connected with merely one spring. In such a case, the movable iron core is separately attached to the belt, and the movable iron core moves following the displacement of the belt.

Figure 9:
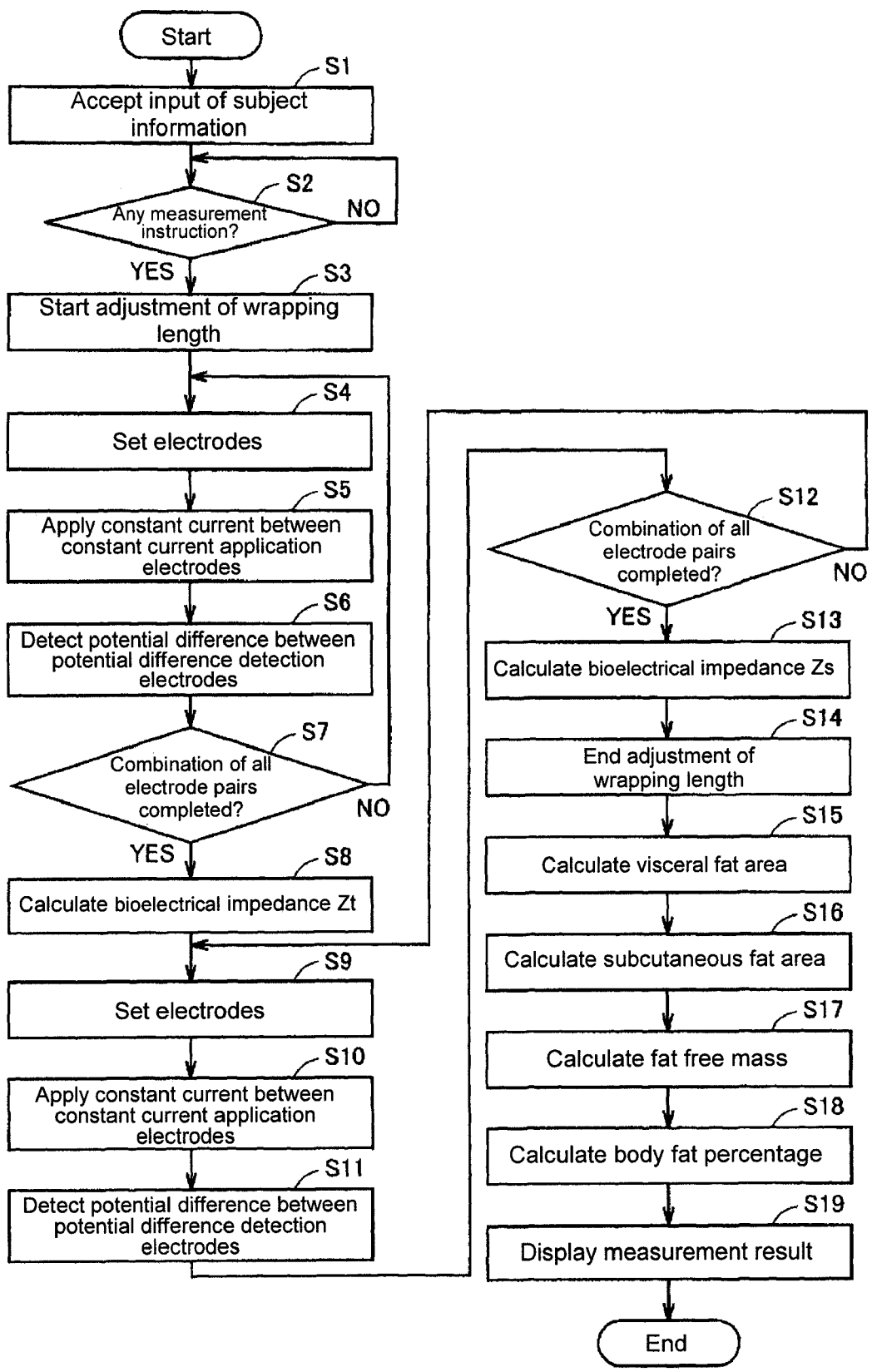
FIG. 9 is a flowchart showing the operation procedures of the body fat measurement device in measuring the visceral fat area, the subcutaneous fat area, and the body fat percentage using the body fat measurement device according to the first embodiment of the present invention.

FIG. 9 is a flowchart showing the operation procedures of the body fat measurement device in measuring the visceral fat area, the subcutaneous fat area, and the body fat percentage using the body fat measurement device according to the present embodiment. The operation of the body fat measurement device 1A in measuring the visceral fat area, the subcutaneous fat area, and the body fat percentage using the body fat measurement device 1A will be described with reference to FIG. 9.

The process shown in the flowchart of FIG. 9 is stored in the memory 29 as program in advance, where the control unit 10 including the calculation processing section 11 reads out and executes the program to realize the functions of the visceral fat area measurement process, the subcutaneous fat area measurement process, and the body fat percentage measurement process. The operation procedures described below are the operation procedures in the case where four sets of abdominal electrode groups, each set including four illustrated abdominal electrodes A11, A12, A21, A22, are arranged parallel to each other in the body fat measurement device shown in FIG. 1.

With reference to FIG. 9, the control unit 10 accepts the input of the subject information containing the waist length W, the height H, the weight Wt and the like serving as physical information (step S1). The accepted subject information is temporarily saved in the memory 29, for example. In the case where a configuration of automatically measuring specific physical information of the subject information using the physical information measurement unit 24 is adopted, the physical information measured by the physical information measurement unit 24 is inputted to the control unit 10.

The control unit 10 determines whether or not an instruction to start the measurement is made (step S2). The control unit 10 waits until the instruction to start the measurement is made (NO in step S2). The control unit 10 starts the automatic adjustment of the wrapping length of the belt 140 (step S3) when detecting the instruction to start the measurement (YES in step S2). Specifically, the wrapping length adjustment mechanism control section 19 of the control unit 10 starts the servo control of the wrapping length adjustment mechanism 32 based on the displacement amount detected by the displacement amount detection unit 30. Preferably, a table and the like stored in the memory 29 in advance, showing the relationship of the displacement amount and the drive signal is used for the servo control.

The control unit 10 then sets the electrode (step S4). In step S4, the control unit 10 selects, for example, a pair of upper limb electrode H11 and lower limb electrode F11 and a pair of upper limb electrode H21 and lower limb electrode F21 as the current electrode pairs, and selects one pair of abdominal electrodes A11, A21 in one abdominal electrode group of the four sets of abdominal electrode groups as the potential difference detection electrode pair. The terminal switching unit 22 electrically connects the pair of upper limb electrode H11 and lower limb electrode F11 and the pair of upper limb electrode H21 and lower limb electrode F21 with the constant current generation unit 21, and electrically connects the pair of abdominal electrodes A11, A21 with the potential difference detection unit 23 based on the control of the control unit 10. The terminal switching unit 22 cuts the electrical connection of the non-selected electrode and the constant current generation unit 21 and the potential difference detection unit 23 based on the control of the control unit 10.

The constant current generation unit 21 flows a constant current between the upper limb and the lower limb based on the control of the control unit 10. For instance, the constant current generation unit 21 flows a constant current from the upper limb electrode H11 and the upper limb electrode H21 to the lower limb electrode F11 and the lower limb electrode F21 (step S5). In this case, the terminal switching unit 22 preferably has a configuration of short circuiting the upper limb electrode H11 and the upper limb electrode H21 and short circuiting the lower limb electrode F11 and the lower limb electrode F21. The constant current generation unit 21 and the terminal switching unit 22 may have a configuration of flowing a constant current from either one of the upper limb electrodes H11, H21 to either one of the lower limb electrodes F11, F21.

In this state, the potential difference detection unit 23 detects the potential difference between the abdominal electrodes A11, A21 based on the control of the control unit 10 (step S6).

The control unit 10 determines whether or not the detection of the potential difference is completed for the combinations of all electrode pairs defined in advance (step S7). The control unit 10 proceeds to step S4 if determined that the detection of the potential difference is not completed for the combination of all of the electrode pairs defined in advance (NO in step S7). The control unit 10 proceeds to step S8, to be hereinafter described, if determined that the detection of the potential difference is completed for the combination of all of the electrode pairs defined in advance (YES in step S7).

In this manner, the control unit 10 selects the abdominal electrodes A11, A21 of another abdominal electrode group in order as the potential difference detection electrode pair. That is, the terminal switching unit 22 electrically connects the abdominal electrodes A11, A21 of another abdominal electrode group with the potential difference detection unit 23 in order based on the control of the control unit 10 (step S4). The potential difference detection unit 23 then detects the potential difference between the abdominal electrodes A11, A21 of another abdominal electrode group in order based on the control of the control unit 10 (step S6).

When the detection of the potential difference is completed for the combination of the abdominal electrodes A11, A21 in all of the abdominal electrode groups (YES in step S7), the impedance measuring portion 12 calculates the bioelectrical impedances Zt1 to Zt4 based on the current value of the constant current generated by the constant current generation unit 21 and flowed through the body and each potential difference detected by the potential difference detection unit 23 (step S8). The values of the bioelectrical impedances Zt1 to Zt4 calculated by the impedance measuring portion 12 are temporarily saved in the memory 29, for example.

The control unit 10 then sets the electrodes again (step S9). More specifically, the control unit 10 selects the pair of abdominal electrodes A11, A21 in one abdominal electrode group of the four sets of abdominal electrode groups as the current application electrode pair, and selects the pair of abdominal electrodes A12, A22 in the abdominal electrode group as the potential difference detection electrode pair. The terminal switching unit 22 electrically connects the pair of abdominal electrodes A11, A21 with the constant current generation unit 21 and electrically connects the pair of abdominal electrodes A12, A22 with the potential difference detection unit 23 based on the control of the control unit 10. Here, the terminal switching unit 22 cuts the electrical connection of the non-selected abdominal electrode, the upper limb electrode and the lower limb electrode and the constant current generation unit 21 and the potential difference detection unit 23 based on the control of the control unit 10.

The constant current generation unit 21 flows a constant current between the abdominal electrodes A11, A21 based on the control of the control unit 10 (step S10).

In this state, the potential difference detection unit 23 detects the potential difference between the abdominal electrodes A12, A22 based on the control of the control unit 10 (step S11).

The control unit 10 determines whether or not the detection of the potential difference is completed for the combinations of all electrode pairs defined in advance (step S12). The control unit 10 proceeds to step S9 if determined that the detection of the potential difference is not completed for the combination of all of the electrode pairs defined in advance (NO in step S12). The control unit 10 proceeds to step S13, to be hereinafter described, if determined that the detection of the potential difference is completed for the combination of all of the electrode pairs defined in advance (YES in step S12).

In this manner, the control unit 10 selects the abdominal electrodes A11, A21 of another abdominal electrode group as the current application electrode pair, and selects the abdominal electrodes A12, A22 in the relevant abdominal electrode group in order as the potential difference detection electrode pair. In other words, the terminal switching unit 22 electrically connects the abdominal electrodes A11, A21 of another abdominal electrode group with the constant current generation unit 21 in order, and electrically connects the abdominal electrodes A12, A22 in the relevant abdominal electrode group with the potential difference detection unit 23 in order based on the control of the control unit 10 (step S9). The potential difference detection unit 23 then flows a constant current between the abdominal electrodes A11, A21 in another abdominal electrode group (step S10), and detects the potential difference between the abdominal electrodes A12, A22 in the relevant abdominal electrode group in order based on the control of the control unit 10 (step S11).

When the application of the current and the detection of the potential difference for the combination of the electrode pairs in all of the abdominal electrode groups are completed (YES in step S12), the impedance measuring portion 12 calculates the bioelectrical impedances Zs1 to Zs4 (step S13) based on the current value of the constant current generated by the constant current generation unit 21 and flowed through the body and each potential difference detected by the potential difference detection unit 23. The values of the bioelectrical impedances Zs1 to Zs4 calculated by the impedance measuring portion 12 are temporarily saved in the memory 29, for example.

The control unit 10 then ends the automatic adjustment of the wrapping length of the belt 140 (step S14).

The visceral fat mass calculating part 16 then calculates the visceral fat area Sv based on the waist length W of the physical information accepted by the control unit 10 in step S1, the calculated bioelectrical impedances Zt1 to Zt4, and the bioelectrical impedances Zs1 to Zs4 (step S15). The visceral fat area Sv is calculated by equation (1). In the case where four sets of abdominal electrode groups, each set including four abdominal electrodes A11, A12, A21, A22, are arranged parallel to each other, the average value of the four bioelectrical impedances Zt1 to Zt4 and the average value of the four bioelectrical impedances Zs1 to Zs4 are respectively substituted to equation (1).

The subcutaneous fat mass calculating part 17 then calculates the subcutaneous fat area Ss based on the waist length W of the physical information accepted by the control unit 10 in step S1, and the calculated bioelectrical impedances Zs1 to Zs4 (step S16). The subcutaneous fat area Ss is calculated by substituting the waist length W and the calculated bioelectrical impedance Zs to equation (2). In the case where four sets of abdominal electrode groups, each set including four abdominal electrodes A11, A12, A21, A22, are arranged parallel to each other, the average value of the four bioelectrical impedances Zs1 to Zs4 is substituted to the bioelectrical impedance Zs of equation (2).

The total fat mass calculating part 14 calculates the fat free mass FFM based on the height H of the physical information accepted by the control unit 10 in step S1 and the calculated bioelectrical impedance Zt (step S17). The fat free mass FFM is calculated by equation (3).

The total fat mass calculating part 14 calculates the body fat percentage based on the weight Wt of the physical information accepted by the control unit 10 in step S1, and the fat free mass FFM calculated by the total fat mass calculating part 14 in step S17 (step S18). The body fat percentage is calculated from equation (4).

The display unit 26 displays each measurement result based on the control of the control unit 10 (step S19).

The body fat measurement device 1A then ends the body fat mass measurement process including the visceral fat area measurement process, the subcutaneous fat area measurement process, and the body fat percentage measurement process. A typical value of the bioelectrical impedances Zt1 to Zt4 is about 5Ω. A typical value of the bioelectrical impedances Zs1 to Zs4 is about 80 Ω.

The bioelectrical impedance measurement abdomen attachment unit 100 can always be attached to the abdomen of the subject with a constant tightening strength in the attached state by configuring the body fat measurement device 1A according to the embodiment as described above, whereby a plurality of electrodes 113 can always be pressed against the abdomen of the subject with a constant load. Through the use of the above-described configuration, the bioelectrical impedance measurement abdomen attachment unit 100 can be closely attached to the abdomen of the subject with satisfactory reproducibility regardless of the waist length of the subject. Furthermore, since the wrapping length of the bioelectrical impedance measurement abdomen attachment unit 100 changes following the breathing motion of the subject by adopting the above-described configuration, the subject does not feel an excessive oppressing feeling, and a bioelectrical impedance measurement abdomen attachment unit that is not painful to the subject is obtained.

Therefore, according to the body fat measurement device 1A of the present embodiment, a body fat measurement device 1A that enables the electrode to be pressed against the body of the subject with a constant load at satisfactory reproducibility in the attached state, and that is not painful to the user is obtained, and the body fat mass can be calculated at high accuracy.

(Second Embodiment)

Figure 10:
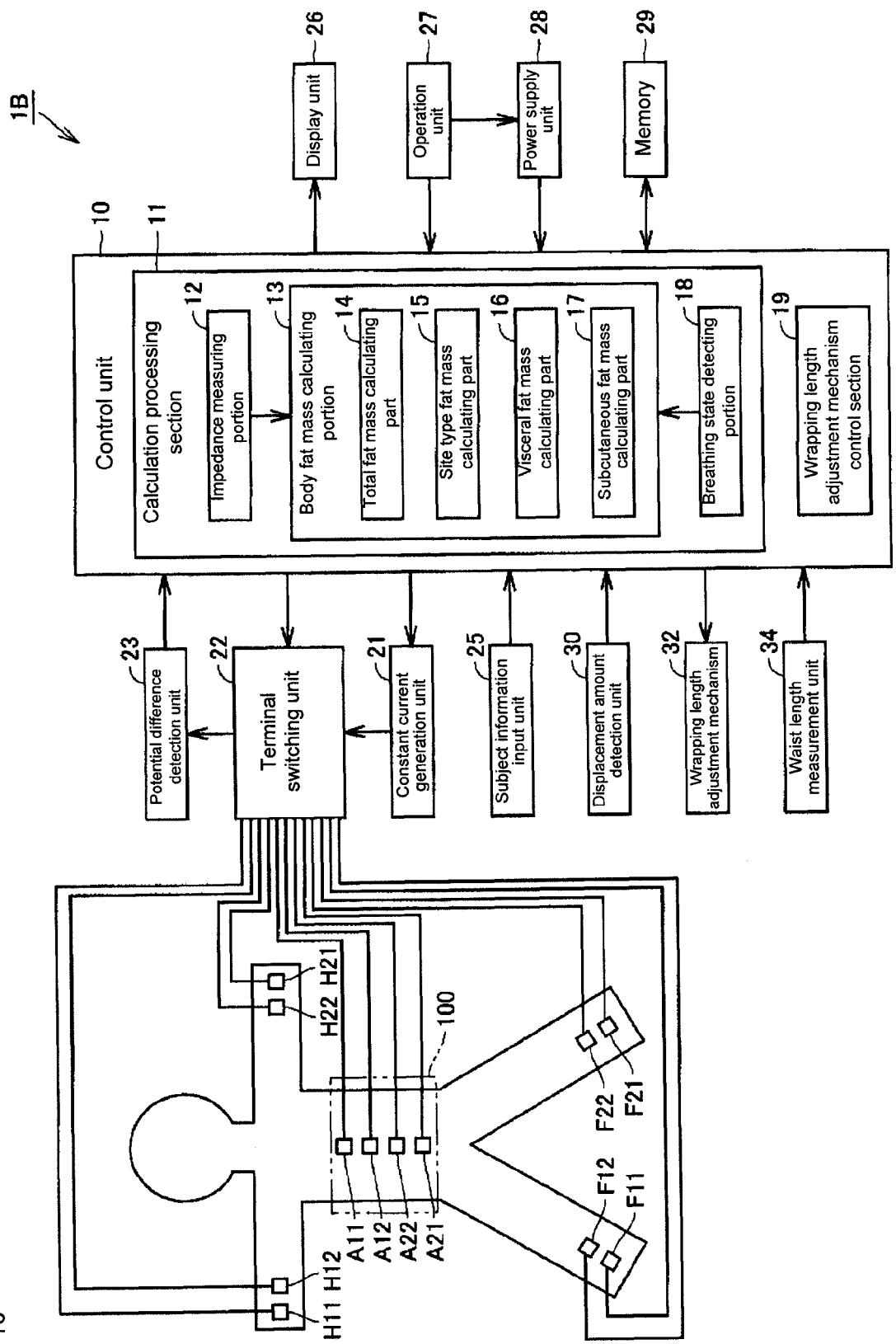
FIG. 10 is a function block diagram of a body fat measurement device in accordance with a second embodiment of the present invention.

FIG. 10 is a view showing function blocks of a body fat measurement device according to a second embodiment of the present invention. First, a configuration of function blocks of a body fat measurement device 1B according to the present embodiment will be described with reference to FIG. 10. The same reference numerals are denoted for the portions similar to the first embodiment, and the description thereof will not be repeated herein.

As shown in FIG. 10, the body fat measurement device 1B according to the present embodiment includes a waist length measurement unit 34 serving as a physical information measurement unit. The waist length measurement unit 34 is a unit for automatically measuring the waist length of the subject, and measures the waist length of the subject based on the output of various sensors arranged in the bioelectrical impedance measurement abdomen attachment unit 100. The waist length of the subject constantly fluctuates, although slightly, with the breathing motion. The waist length measurement unit 34 constantly measures the fluctuating waist length during the measurement, and measures the waist length of the subject by detecting the wrapping length of the belt wrapped around the body of the subject and also measures the fluctuation of the waist length of the subject by detecting the fluctuation of the wrapping length of the belt wrapped around the body of the subject. In other words, the waist length measurement unit 34 has functions of both the body peripheral length measurement unit and the body peripheral length fluctuation amount measurement unit. The waist length measurement unit 34 outputs the information of the measured waist length and the information of the fluctuation thereof to the control unit 10. In this case, the waist length is the body peripheral length of the portion including the umbilicus position of the subject.

In the body fat measurement device 1B according to the present embodiment, the calculation processing section 11 includes a breathing state detecting portion 18 in addition to the impedance measuring portion 12 and the body fat mass calculating portion 13. The breathing state detecting portion 18 detects the breathing state of the subject during the measurement operation based on the information of the waist length of the subject measured by the waist length measurement unit 34 and inputted to the control unit 10. The body fat mass calculating portion 13 calculates the body fat mass based on the bioelectrical impedance obtained in the impedance measuring portion 12, the information of the breathing state obtained in the breathing state detecting portion 18, and the subject information inputted from the physical information measurement unit 24 and/or the subject information input unit 25.

Figure 11:
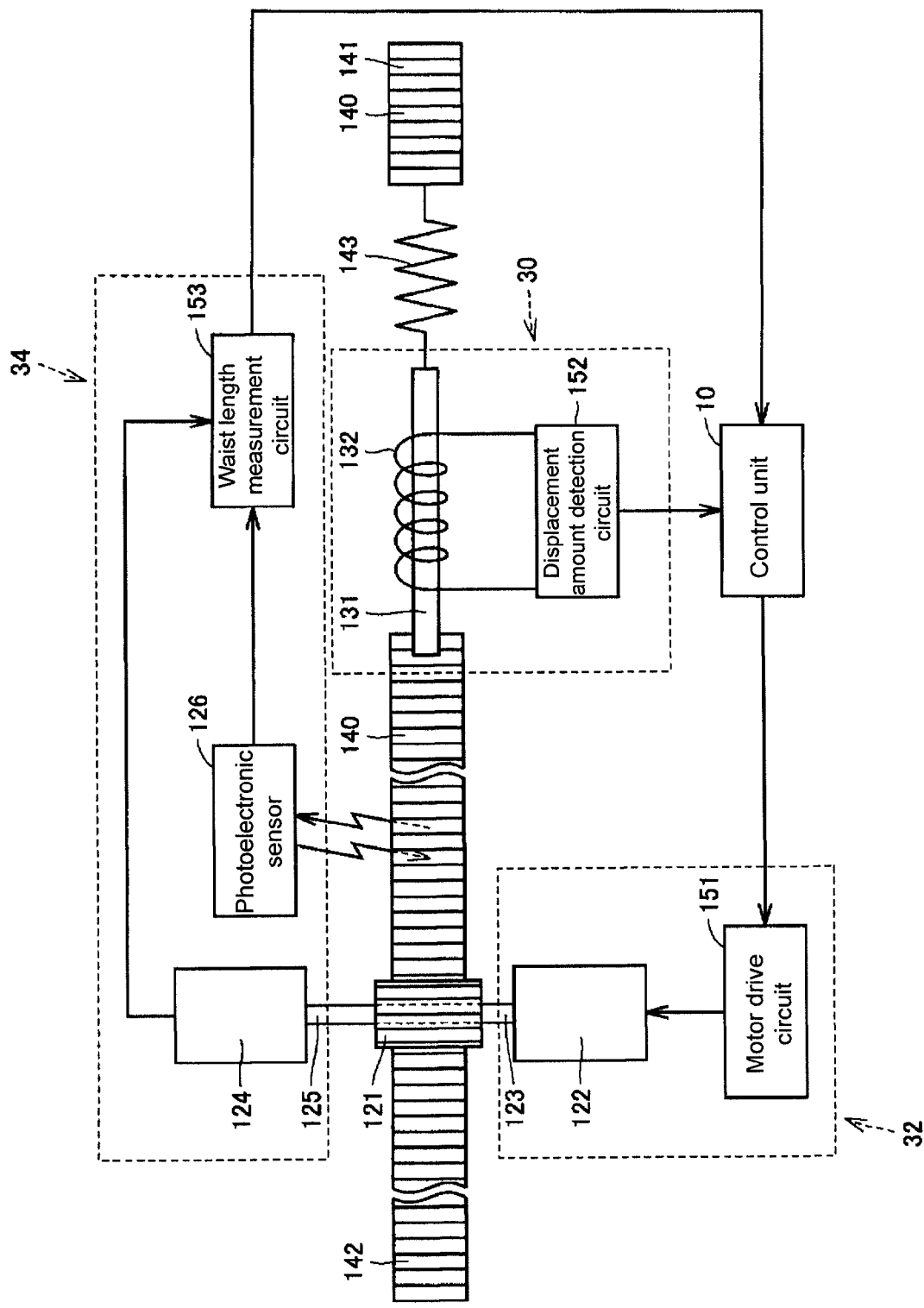
FIG. 11 is a function block diagram showing a specific configuration of a wrapping length adjustment unit and a waist length measurement unit of a body fat measurement device according to a second embodiment of the present invention.
Figure 12:
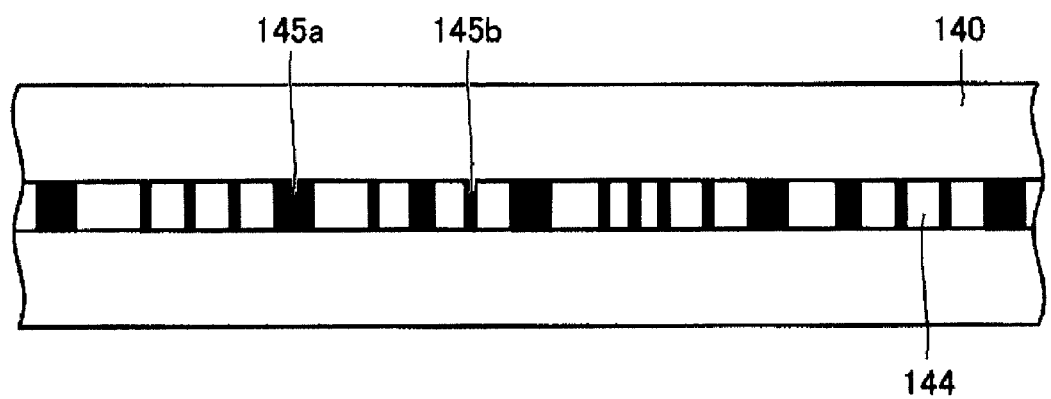
FIG. 12 is a bottom view of a belt of a bioelectrical impedance measurement abdomen attachment unit according to the second embodiment of the present invention.
Figure 13:
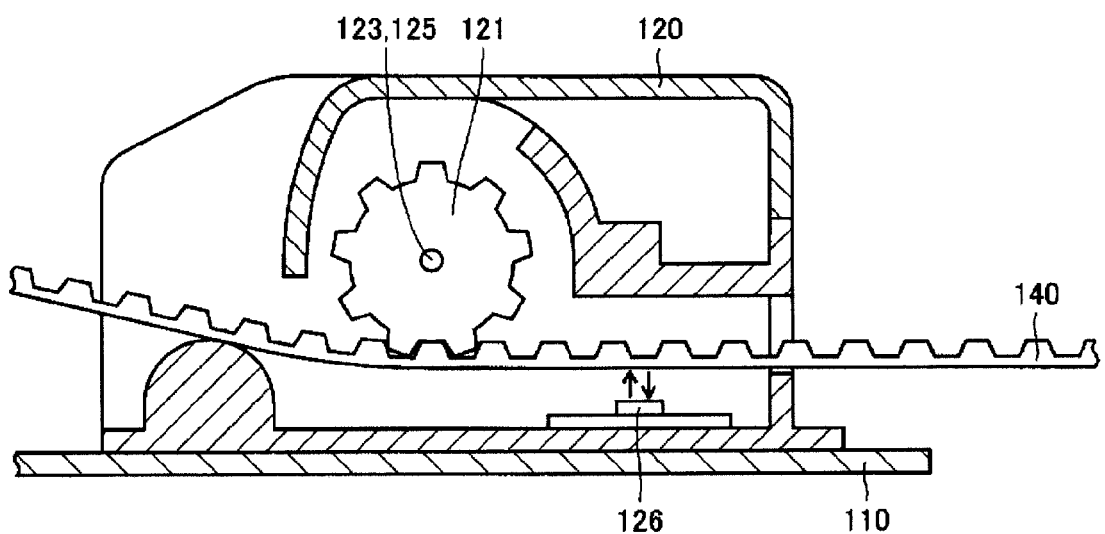
FIG. 13 is a perspective view showing a structure of a holder of the bioelectrical impedance measurement abdomen attachment unit according to the second embodiment of the present invention.

FIG. 11 is a function block diagram showing a specific configuration of the waist length measurement unit of the body fat measurement device according to the present embodiment. FIG. 12 is a bottom view of the belt of the bioelectrical impedance measurement abdomen attachment unit according to the present embodiment, and FIG. 13 is a schematic cross-sectional view of the holder. The specific configuration of the waist length measurement unit according to the present embodiment will be specifically described with reference to FIGS. 11 to 13. The same reference numerals are denoted for the portions similar to the first embodiment, and the description thereof will not be repeated.

As shown in FIG. 11, the waist length measurement unit 34 includes a photoelectronic sensor 126 and a rotary encoder 124 serving as a sensor for detecting the position of the belt 140 of the bioelectrical impedance measurement abdomen attachment unit 100, and a waist length measurement circuit 153. Each of the photoelectronic sensor 126 and the rotary encoder 124 is arranged in the holder 120 of the bioelectrical impedance abdomen attachment unit 100. Specifically, as shown in FIG. 13, the photoelectronic sensor 126 is arranged on the bottom surface of the casing of the holder 120 fixed on the electrode support 110 side, where the belt 140 passes the upper side thereof. The rotary encoder 124 is arranged in the holder 120 such that a detection shaft 125 is fixed to the pulley with teeth 121.

As shown in FIG. 12, an encoder strip 144 is attached to the lower surface of the belt 140 (main surface on the side facing the abdomen of the subject in the attached state, and the surface on the side not formed with teeth). The encoder strip 144 is arranged to extend from the other end 142 of the belt 140 to a predetermined position of the one end 141, where an identifier (barcode elements 145a, 145b, and the like, herein) indicating an absolute position of the belt 140 is arranged on the surface thereof. The encoder strip 144 is arranged facing the photoelectronic sensor 126, described above, in the holder 120.

The photoelectronic sensor 126 includes a light emitting unit and a light receiving unit, where light emitted from the light emitting unit is applied on the encoder strip 144 and the reflected light is received by the light receiving unit. The photoelectronic sensor 126 outputs an electrical signal by photoelectrically converting the received light, and inputs the same to the waist length measurement circuit 153. The waist length measurement circuit 153 detects the position of the belt 140 of the portion arranged facing the photoelectronic sensor 126 based on the inputted electrical signal, detects the wrapping length of the belt 140 wrapped around the abdomen of the subject based on the positional information, and specifies the waist length of the subject based thereon.

The rotary encoder 124 detects the rotation angle of the pulley with teeth 121 that rotates when the belt 140 is fed out when the detection shaft 125 rotates. The rotary encoder 124 outputs an electrical signal corresponding to the detected rotation angle, and inputs the same to the waist length measurement circuit 153. The waist length measurement circuit 153 detects the feeding amount of the belt 140 based on the inputted electrical signal, and specifies the fluctuation amount of the wrapping length involved in the breathing motion of the belt 140 wrapped around the abdomen of the subject based thereon.

The waist length measurement circuit 153 outputs the waist length and the fluctuation amount of the wrapping length specified using the photoelectronic sensor 126 and the rotary encoder 124 to the control unit 10.

In the present embodiment, the waist length of the subject is specified based on the information detected by the photoelectronic sensor 126, and the fluctuation amount of the waist length of the subject is specified based on the information detected by the rotary encoder 124, but the information detected by the rotary encoder 124 may be used to specify the waist length of the subject, and the information detected by the photoelectronic sensor 126 may be used to specify the fluctuation amount of the waist length of the subject.

An example of a calculation process carried out in the body fat measurement device 1B according to the present embodiment will now be described. In the body fat measurement device 1B according to the present embodiment as well, the calculation process basically the same as the body fat measurement device 1A according to the first embodiment is carried out, but the value of the waist length actually measured by the waist length measurement unit 34 is used for the value of the waist length W, and the values of the bioelectrical impedances Zt, Zs obtained in association with the information of the breathing state detected by the breathing state detecting portion 18 are used for the values of the bioelectrical impedances Zt, Zs used in various calculation processes.

The impedance measuring portion 12 calculates two types of bioelectrical impedances Zt, Zs based on the current value of the constant current generated by the constant current generation unit 21 and the potential difference detected by the potential difference detection unit 23, but the bioelectrical impedance Zt that reflects the fat free mass at the abdomen of the subject and the bioelectrical impedance Zs that reflects the subcutaneous fat mass at the abdomen of the subject both vary from hour to hour according to the breathing motion of the subject.

Figure 14:
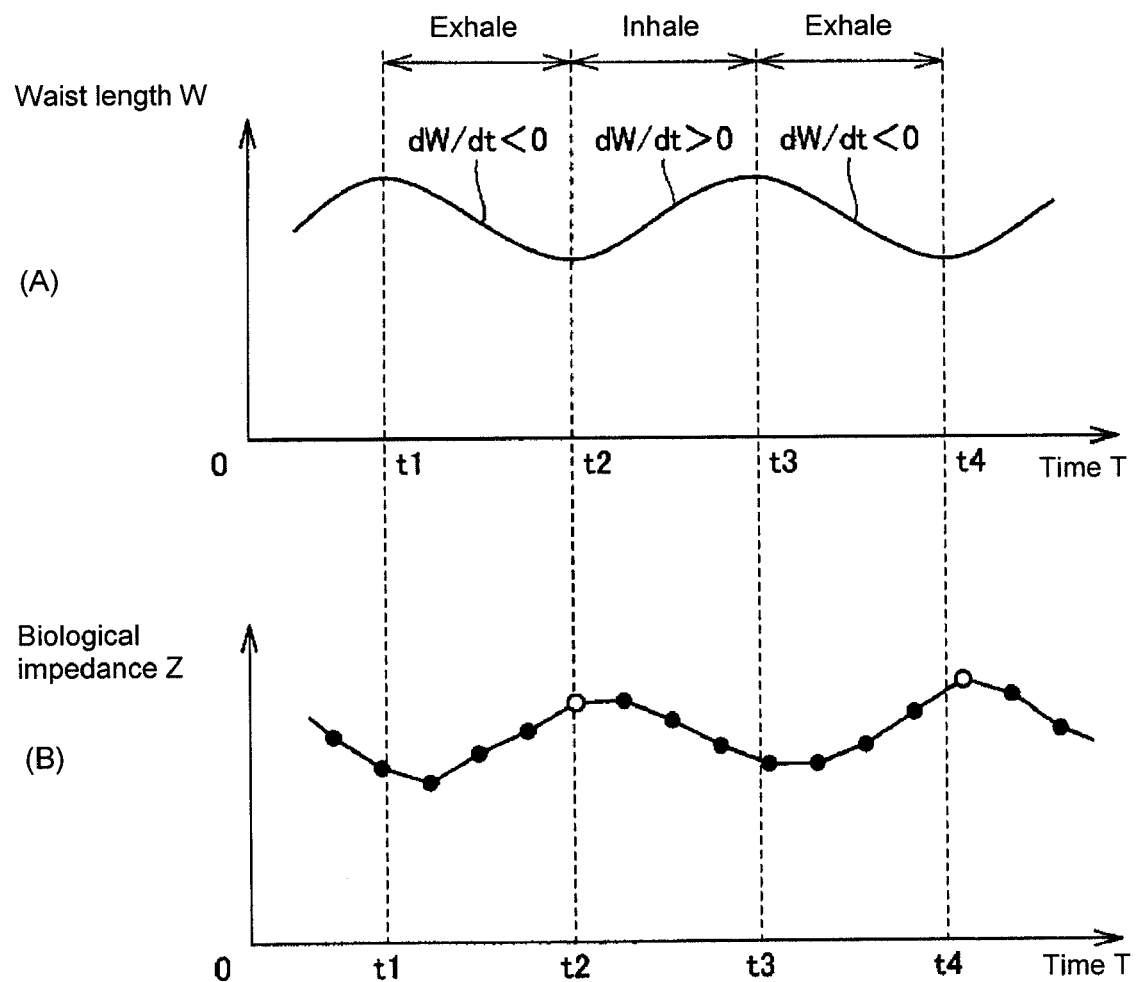
FIG. 14 is a graph showing a relationship of a fluctuation of a waist length of the subject and a bioelectrical impedance that varies from hour to hour.

FIG. 14 is a graph showing a relationship of the fluctuation of the waist length of the subject and the bioelectrical impedance that varies from hour to hour. In FIG. 14, a horizontal axis indicates time, where a vertical axis of a portion (A)

indicates the waist length and a vertical axis of a portion (B) indicates the bioelectrical impedance.

As shown in the portion (A) of FIG. 14, the waist length W of the subject fluctuates in accordance with the breathing motion of the subject, where the waist length W increases when the subject performs the inhaling motion and the waist length W decrease when the subject performs the exhaling motion. On the contrary, the bioelectrical impedance Z also fluctuates in accordance with the breathing motion of the subject as shown in the portion (B) of FIG. 14, where the value generally decreases when the subject performs the inhaling motion and the value generally increases when the subject performs the exhaling motion.

In the body fat measurement device 1B according to the present embodiment, the following processes are performed on the acquired data to exclude such a fluctuation involved in the breathing motion of the bioelectrical impedance Z as an error component. First, for a predetermined period defined in advance, the potential difference between the potential difference detection electrodes is measured by the potential difference detection unit 23 over a plurality of times at a predetermined interval, and the data of the obtained potential difference is acquired as time-series data. The time-series data of the bioelectrical impedance Z is then obtained from the time-series data of the potential difference obtained by the impedance measuring portion 12. In parallel thereto, the waist length W of the subject of a period same as the period in which the detection of the potential difference is carried out is acquired as time-series data by the waist length measurement unit 34.

The time-series data of the acquired bioelectrical impedance Z and the time-series data of the waist length W are then synchronized. Thereafter, dW/dt at each time is calculated based on the time-series data of the waist length W in the breathing state detecting portion 18. If the calculated dW/dt takes a positive value (i.e., dW/dt>0), the subject is determined as performing the exhaling motion (e.g., period of t2 to t3 shown in the portion (A) of FIG. 14), whereas if the calculated dW/dt takes a negative value (i.e., dW/dt<0), the subject is determined as performing the inhaling motion (e.g., period of t1 to t2, t3 to t4 shown in the portion (A) of FIG. 14). The time of transitioning from the exhaling motion to the inhaling motion (i.e., time at which dW/dt=0, or time at which dW/dt changes from a negative value to a positive value) is then specified (e.g., time t2, t4 shown in the portion (A) of FIG. 14).

The bioelectrical impedance (e.g., bioelectrical impedance shown with an outlined circle in the portion (B) of FIG. 14) acquired at the time closest to or the time same as the time of transitioning from the exhaling motion to the inhaling motion is extracted from the time-series data of the bioelectrical impedance Z, and the average value of the extracted data is decided as a representative value of the bioelectrical impedance Z. The average value of the waist length acquired at the time closest to or the time same as the time of transitioning from the exhaling motion to the inhaling motion is decided as a representative value of the waist length W of the subject.

The method of deciding the representative value of the bioelectrical impedance described above merely shows one example. A case of using the bioelectrical impedance acquired at the timing of transitioning from the exhaling motion to the inhaling motion as the representative value has been shown, but the bioelectrical impedance acquired at the timing of transitioning from the inhaling motion to the exhaling motion may be used as the representative value. Instead of simply extracting specific data from the time-series data of the bioelectrical impedance Z and obtaining the average value thereof to decide the representative value, other calculations or the like may be added to decide the representative value. In either case, the representative value of the bioelectrical impedance Z merely needs to be decided in association with the breathing motion of the subject detected from the fluctuation of the waist length of the subject.

In the body fat measurement device 1B according to the present embodiment, various types of fat mass are calculated using the representative value of the waist W and the representative values of the bioelectrical impedances Zt, Zs obtained in the above manner. Equations (1) to (4) shown in the first embodiment are used for the equations for calculating the same.

Figure 15:
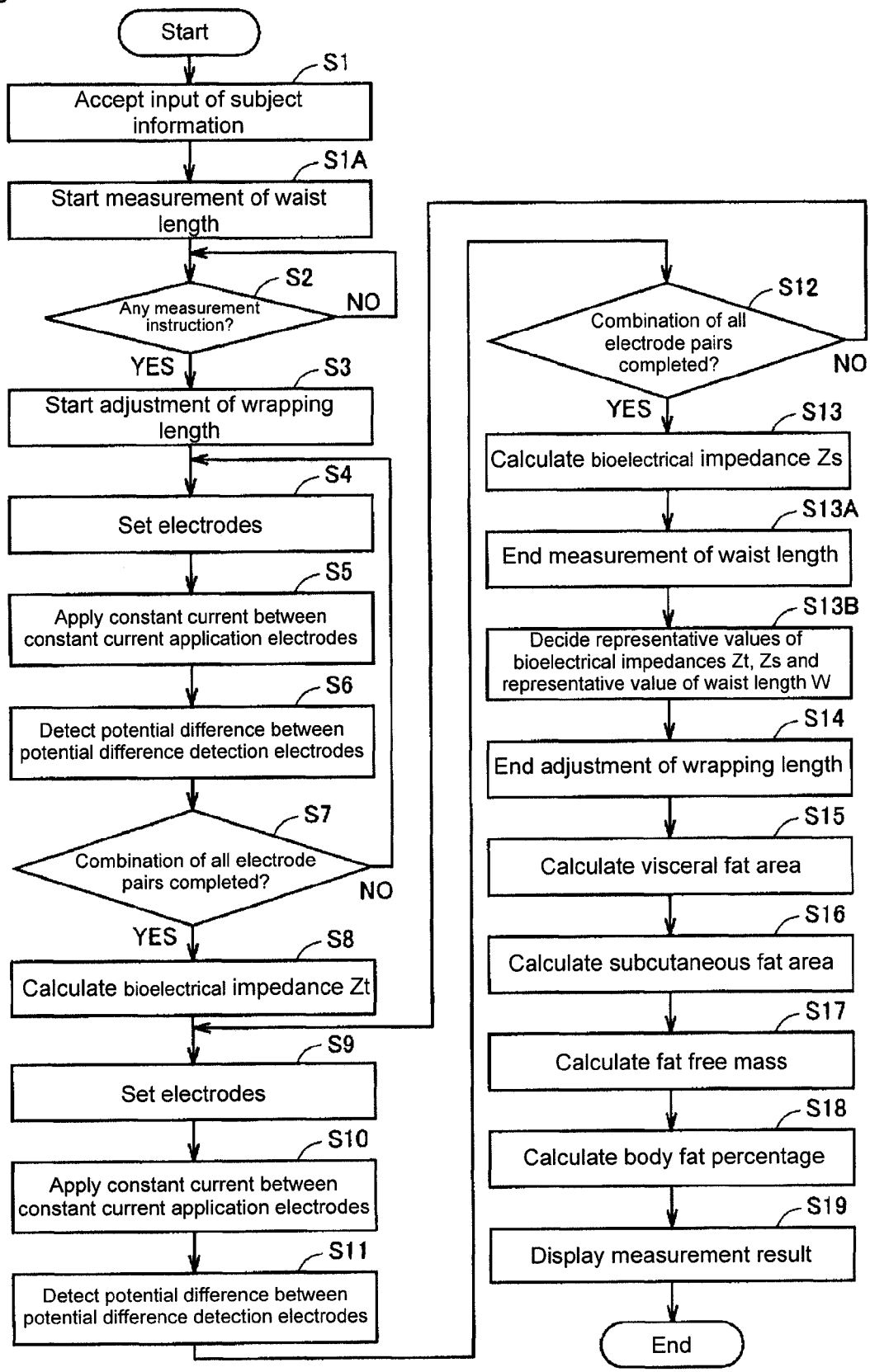
FIG. 15 is a flowchart showing the operation procedures of the body fat measurement device in measuring the visceral fat area, the subcutaneous fat area, and the body fat percentage using the body fat measurement device according to the second embodiment of the present invention.

FIG. 15 is a flowchart showing the operation procedures of the body fat measurement device in measuring the visceral fat area, the subcutaneous fat area, and the body fat percentage using the body fat measurement device according to the present embodiment. In the figure, the same step numbers are denoted for the steps similar to the first embodiment, and the detailed description thereof will not be repeated herein.

With reference to FIG. 15, the control unit 10 accepts the input of the height H, the weight Wt and the like as physical information other than the waist length W (step S1). The accepted subject information is temporarily saved in the memory 29.

The control unit 10 then outputs a command to start the measurement of the waist length to the waist length measurement unit 34, and the waist length measurement unit 34 starts the measurement of the waist length W based thereon (step S1A).

The control unit 10 determines whether or not an instruction to start the measurement is made (step S2). The control unit 10 waits until the instruction to start the measurement is made (NO in step S2). The control unit 10 starts the automatic adjustment of the wrapping length of the belt 140 (step S3) when detecting the instruction to start the measurement (YES in step S2).

The control unit 10 then sets the electrode (step S4), and the constant current generation unit 21 flows a constant current between the upper limb and the lower limb based on the control of the control unit 10 (step S5). In this state, the potential difference detection unit 23 detects the potential difference between the abdominal electrodes serving as the selected potential difference detection electrode over a plurality of times at a predetermined interval for a predetermined period defined in advance based on the control of the control unit 10 (step S6).

The control unit 10 determines whether or not the detection of the potential difference is completed for the combinations of all abdominal electrode pairs serving as the potential difference detection electrode defined in advance (step S7). The control unit 10 proceeds to the process of step S4 if determined that the detection of the potential difference is not completed for the combination of all of the abdominal electrode pairs serving as the potential difference detection electrode defined in advance (NO in step S7), and selects the non-selected abdominal electrode pair. The control unit 10 thereby detects, in order, the potential difference between the abdominal electrodes of the potential difference detection electrode pair of a plurality of pairs.

When the detection of the potential difference is completed for the combination of the abdominal electrode pairs serving as the potential difference detection electrode pair defined in advance (YES in step S7), the impedance measuring portion 12 calculates the time-series data of the bioelectrical impedances Zt1 to Zt4 based on the current value of the constant current generated by the constant current generation unit 21 and flowed through the body and the time-series data of each potential difference detected by the potential difference detection unit 23 (step S8). The time-series data of the bioelectrical impedances Zt1 to Zt4 calculated by the impedance measuring portion 12 is associated with the time-series data of the waist length W measured by the waist length measurement unit 34, and temporarily saved in the memory 29.

The control unit 10 then sets the electrodes again (step S9), and the constant current generation unit 21 flows a constant current between the abdominal electrodes serving as the selected constant current application electrode based on the control of the control unit 10 (step S10). In this state, the potential difference detection unit 23 detects the potential difference between the abdominal electrodes serving as the selected potential difference detection electrode over a plurality of times at a predetermined interval for a predetermined period defined in advance based on the control of the control unit 10 (step S11).

The control unit 10 determines whether or not the application of the constant current and the detection of the potential difference are completed for all of the combinations of the constant current application electrode pairs and the potential difference detection electrode pairs defined in advance (step S12). The control unit 10 proceeds to the process of step S9 if determined that the application of the constant current and the detection of the potential difference are not completed for all of the combinations of the constant current application electrode pairs and the potential difference detection electrode pairs defined in advance (NO in step S12), and selects the non-selected electrode pair. In this manner, the control unit 10 performs constant current application and potential difference detection, in order, on all of the combinations of the constant current application electrode pair and the potential difference detection electrode pair defined in advance.

When the application of the constant current and the detection of the potential difference are completed for all of the combinations of the constant current application electrode pairs and the potential difference detection electrode pairs defined in advance (YES in step S12), the impedance measuring portion 12 calculates the time-series data of the bioelectrical impedances Zs1 to Zs4 based on the current value of the constant current generated by the constant current generation unit 21 and flowed through the body and the time-series data of each potential difference detected by the potential difference detection unit 23 (step S13). The time-series data of the bioelectrical impedances Zs1 to Zs4 calculated by the impedance measuring portion 12 is associated with the time-series data of the waist length W measured by the waist length measurement unit 34, and temporarily saved in the memory 29.

The control unit 10 then outputs a command to end the measurement of the waist length to the waist length measurement unit 34, and the waist length measurement unit 34 ends the measurement of the waist length W based thereon (step S13A). Thereafter, the body fat mass calculating portion 13 decides the representative values of the bioelectrical impedances Zt1 to Zt4 and the bioelectrical impedances Zs1 to Zs4 and decides the representative value of the waist length W based on the time-series data of the bioelectrical impedances Zt1 to Zt4 and the time-series data of the bioelectrical impedances Zs1 to Zs4, which are temporarily saved in the memory 29 and associated with the times-series data of the waist length W (step S13B). The method of deciding the representative value is as described above.

The control unit 10 then ends the automatic adjustment of the wrapping length of the belt 140 (step S14).

The visceral fat mass calculating part 16 then calculates the visceral fat area Sv based on the representative value of the actually measured waist length W, the representative value of the calculated bioelectrical impedances Zt1 to Zt4, and the representative value of the bioelectrical impedances Zs1 to Zs4 (step S15). The visceral fat area Sv is calculated from equation (1). In the case where four sets of abdominal electrode groups, each set including four abdominal electrodes A11, A12, A21, A22, are arranged parallel to each other as mentioned above, the average value of the representative values of the four bioelectrical impedances Zt1 to Zt4 and the average value of the representative values of the four bioelectrical impedances Zs1 to Zs4, for example, are respectively substituted to equation (1).

The subcutaneous fat mass calculating part 17 then calculates the subcutaneous fat area Ss based on the representative value of the actually measured waist length W, and the representative value of the calculated bioelectrical impedances Zs1 to Zs4 (step S16). The subcutaneous fat area Ss is calculated by substituting the waist length W and the calculated bioelectrical impedance Zs to equation (2). In the case where four sets of abdominal electrode groups, each set including four abdominal electrodes A11, A12, A21, A22, are arranged parallel to each other as mentioned above, the average value of the representative values of the four bioelectrical impedances Zs1 to Zs4, for example, is substituted to the bioelectrical impedance Zs in equation (2).

The total fat mass calculating part 14 calculates the fat free mass FFM based on the height H of the physical information accepted by the control unit 10 in step S1 and the representative value of the calculated bioelectrical impedance Zt (step S17). The fat free mass FFM is calculated by equation (3). In the case where four sets of abdominal electrode groups, each set including four abdominal electrodes A11, A12, A21, A22, are arranged parallel to each other as mentioned above, the average value of the representative values of the four bioelectrical impedances Zt1 to Zt4, for example, is substituted to the bioelectrical impedance Zt in equation (3).

The total fat mass calculating part 14 calculates the body fat percentage based on the weight Wt of the physical information accepted by the control unit 10 in step S1, and the fat free mass FFM calculated by the total fat mass calculating part 14 in step S17 (step S18). The body fat percentage is calculated from equation (4).

The display unit 26 displays each measurement result based on the control of the control unit 10 (step S19).

The body fat measurement device 1B then ends the body fat mass measurement process including the visceral fat area measurement process, the subcutaneous fat area measurement process, and the body fat percentage measurement process.

By adopting the configuration of the body fat measurement device 1B according to the present embodiment described above, an effect in that the waist length of the subject 300 can be automatically measured with a simple configuration of detecting the wrapping length of the belt 140 of the bioelectrical impedance measurement abdomen attachment unit 100 at the time of measurement is obtained in addition to the effects described in the first embodiment. Therefore, a body fat measurement device capable of measuring the body fat at high accuracy by calculating the body fat mass using the information of the actually measured waist length is obtained.

Furthermore, with the above-described configuration, the breathing state of the subject 300 can be detected at high accuracy with a simple configuration of detecting the fluctuation of the wrapping length of the belt 140 of the bioelectrical impedance measurement abdomen attachment unit 100 at the time of measurement. Through the use of such a detection method, the change in waist length of the subject 300 involved in the breathing motion can be captured at high accuracy. Thus, the bioelectrical impedance can be accurately measured excluding the influence of the fluctuation of the bioelectrical impedance that occurs with the breathing motion by acquiring the value of the bioelectrical impedance as the time-series data using the above-described detection method, and associating the same with the breathing motion of the subject 300 to decide the representative value of the bioelectrical impedance. As a result, a body fat measurement device capable of measuring the body fat mass at high accuracy can be inexpensively manufactured. In particular, since the bioelectrical impedance needs to be measured with the electrode 113 arranged in contact with the abdomen 301 of the subject 300 in order to measure the visceral fat mass and the subcutaneous fat mass at the abdomen at high accuracy, the visceral fat mass and the subcutaneous fat mass at the abdomen can be calculated at high accuracy with the body fat measurement device 1B of the above configuration.

In the first and second embodiments of the present invention described above, the case where the electrode is arranged in contact with the front surface of the abdomen of the subject has been described, but the present invention is also applicable to a body fat measurement device configured to arrange the electrodes so as to come in contact with the back surface of the abdomen or the side (flank) of the subject, and a bioelectrical impedance measurement abdomen attachment unit arranged therein.

In the first and second embodiments of the present invention described above, the case where the belt with teeth is used for the belt has been described, but it can be recognized that a belt without teeth may also be used as the belt. In such a case, a pulley without teeth is used for the pulley provided at the holder, and a mechanism for holding the belt by friction or the like and sending out the belt is adopted for the wrapping length adjustment mechanism provided at the holder.

In the second embodiment of the present invention described above, the case where the waist length measurement unit has a configuration of detecting not only the waist length of the subject but also the fluctuation amount thereof has been described, but a configuration of obtaining even the fluctuation amount of the waist length is not always necessary, and may not be carried out in order to simplify the device.

In the first and second embodiments of the present invention, a body fat measurement device in which the electrode is intended to be arranged in contact with the four limbs of the subject using the impedance measurement upper limb attachment unit and the lower limb attachment unit has been described, but the application of the present invention is not limited to such a body fat measurement device, and may be applied to a body fat measurement device in which the electrode is not arranged in contact with the four limbs and the electrode is intended to be arranged in contact with only the body (abdomen).

Furthermore, in the first and second embodiments of the present invention, the case where the present invention is applied to a body fat measurement device in which the subject is intended to take the laid position at the time of measurement and a bioelectrical impedance measurement abdomen attachment unit arranged therein has been described, but the present invention is also applicable to a body fat measurement device in which the subject is intended to take the posture other than the laid position such as a face-down position, a side position, a standing position and a sitting position, and a bioelectrical impedance measurement abdomen attachment unit arranged therein.

The embodiments disclosed herein are illustrative in all aspects and should not be construed as being restrictive. The scope of the invention is defined by the claims, and all modifications equivalent in meaning to the claims and within the scope thereof are intended to be encompassed therein.

The invention claimed is:

1. A body fat measurement device comprising:
 a bioelectrical impedance measurement body attachment unit including a plurality of electrodes arranged in contact with a body of a subject in an attached state;
 an impedance measuring portion for measuring a bioelectrical impedance of the subject using the plurality of electrodes; and
 a body fat mass calculating portion for calculating a body fat mass of the subject based on the bioelectrical impedance measured by the impedance measuring portion; wherein
 the bioelectrical impedance measurement body attachment unit includes an electrode support for supporting the plurality of electrodes and a long belt to be wrapped around the body of the subject in the attached state to attach the electrode support to the body of the subject;
 the belt includes, in least at one part, a stretchable region that stretches in a length direction;
 the electrode support includes a fixing portion fixed with one end of the belt in a relatively immovable manner with respect to the electrode support and a holder for holding a portion closer to the other end of the belt in a relatively movable manner with respect to the electrode support in the attached state;
 the holder includes a wrapping length adjustment mechanism for adjusting a wrapping length of the belt; and
 the body fat measurement device further includes,
 a displacement amount detection unit for detecting a displacement amount in the length direction of the belt caused by the stretching of the stretchable region, and
 a wrapping length adjustment mechanism control section for automatically adjusting the wrapping length of the belt by controlling the wrapping length adjustment mechanism based on information detected by the displacement amount detection unit
 wherein the wrapping length adjustment control section extends the belt when the detected displacement amount of the stretchable region determined by the displacement amount detection unit surpasses a predetermined value and the wrapping length adjustment control section retracts the belt when the detected displacement amount of the stretchable region determined by the displacement amount detection unit goes below the predetermined value.

2. The body fat measurement device according to claim 1, wherein the wrapping length of the belt is adjusted during an attachment task of attaching the bioelectrical impedance measurement body attachment unit to the body of the subject.

3. The body fat measurement device according to claim 1, wherein the wrapping length of the belt is constantly adjusted during a measurement operation of the bioelectrical impedance.

4. The body fat measurement device according to claim 1, further comprising:
 a body peripheral length measurement unit for measuring a body peripheral length of the subject by detecting a wrapping length of the belt wrapped around the body of the subject with the bioelectrical impedance measurement body attachment unit attached to the body of the subject; wherein the body fat mass calculating portion calculates the body fat mass of the subject based on the bioelectrical impedance measured by the impedance measuring portion and the body peripheral length of the subject measured by the body peripheral length measurement unit.

5. The body fat measurement device according to claim 1, further comprising:
- a body peripheral length fluctuation amount measurement unit for detecting fluctuation of a body peripheral length of the subject by detecting fluctuation of the wrapping length of the belt wrapped around the body of the subject with the bioelectrical impedance measurement body attachment unit attached to the body of the subject; and
- a breathing state detecting portion for detecting a breathing state of the subject based on the fluctuation of the body peripheral length of the subject measured by the body peripheral length fluctuation amount measurement unit; wherein the body fat mass calculating portion calculates the body fat mass of the subject based on the bioelectrical impedance measured by the impedance measuring portion and information on the breathing state detected by the breathing state detecting portion.

6. The body fat measurement device according to claim 5, wherein the body fat calculating portion extracts the bioelectrical impedance measured at a timing of transitioning from an exhaling motion to an inhaling motion detected by the breathing state detecting portion from time-series data of the bioelectrical impedance measured by the impedance measuring portion, and calculates the body fat mass of the subject from the extracted bioelectrical impedance.

7. The body fat measurement device according to claim 1, wherein the body fat mass calculating portion includes a visceral fat mass calculating part for calculating a visceral fat mass of the subject.

8. The body fat measurement device according to claim 1, wherein the body fat mass calculating portion includes a subcutaneous fat mass calculating part for calculating a subcutaneous fat mass at an abdomen of the subject.

* * * * *